United States Patent
Kreitman et al.

(10) Patent No.: US 6,448,436 B1
(45) Date of Patent: Sep. 10, 2002

(54) INTEGRATED PROCESS FOR THE PRODUCTION OF 2, 6-NAPHTHALENE DICARBOXYLIC ACID

(75) Inventors: Keith Michael Kreitman; Steve Edward Brewer; John Bernard Rodden; Robert Lawrence Blackbourn; Thomas Fairchild Brownscombe; James Laurel Buechele, all of Houston; Ye-Mon Chen, Sugar Land; Zaida Diaz, Houston; Donn Anthony DuBois, Houston, all of TX (US); Raymond Lawrence June, Singapore (SG); Brendan Dermot Murray, Houston; Michael Wayne Potter, Sugar Land, both of TX (US)

(73) Assignee: Mossi & Ghisolfi Overseas, S. A., Luxembourg (LU)

( * ) Notice: Subject to any disclaimer, the term of this patent is extended or adjusted under 35 U.S.C. 154(b) by 0 days.

(21) Appl. No.: 09/644,003
(22) Filed: Aug. 22, 2000

Related U.S. Application Data

(60) Provisional application No. 60/151,577, filed on Aug. 30, 1999.

(51) Int. Cl.[7] .............................................. C07C 51/265
(52) U.S. Cl. ....................................... 562/412; 562/414
(58) Field of Search ................................. 562/412, 414

(56) References Cited

U.S. PATENT DOCUMENTS

| | | | |
|---|---|---|---|
| 2,823,231 A | 2/1958 | Raecke et al. ............... | 260/515 |
| 2,833,816 A | 5/1958 | Safer et al. .................. | 260/524 |
| 2,849,482 A | 8/1958 | Raecke et al. ............... | 260/515 |
| 2,927,130 A | 3/1960 | Schitt et al. ................. | 260/525 |
| 2,948,750 A * | 8/1960 | Blaser et al. | |
| 3,449,070 A | 6/1969 | McDaniel et al. ............ | 23/111 |
| 3,631,096 A | 12/1971 | Kuper ..................... | 260/515 P |
| 3,671,578 A | 6/1972 | Ogata et al. ............. | 260/515 P |
| 3,766,258 A | 10/1973 | Engelbrecht et al. .... | 260/515 P |
| 3,856,855 A | 12/1974 | Yamashita et al. ...... | 260/524 R |
| 3,870,754 A | 3/1975 | Yamashita et al. ...... | 260/524 R |
| 3,888,921 A | 6/1975 | Yamamoto et al. ......... | 260/525 |
| 3,952,052 A | 4/1976 | Sherk .......................... | 260/525 |
| 4,263,451 A | 4/1981 | Lewis et al. ................. | 562/481 |
| 4,430,511 A | 2/1984 | Wu .............................. | 562/481 |
| 4,455,220 A | 6/1984 | Parker et al. ................ | 208/161 |
| 4,820,868 A | 4/1989 | Mitamura et al. ........... | 562/482 |
| 4,886,901 A | 12/1989 | Holzhauer et al. ............ | 560/77 |
| 4,933,491 A | 6/1990 | Albertins et al. ............ | 562/416 |
| 4,950,786 A | 8/1990 | Sanchez et al. ............. | 562/416 |
| 5,254,719 A | 10/1993 | Holzhaver et al. ............ | 560/78 |

(List continued on next page.)

FOREIGN PATENT DOCUMENTS

| | | | |
|---|---|---|---|
| CA | 864587 | 2/1971 | ................. 260/521 |
| GB | 1472777 | 5/1977 | |
| JP | 56020051 B4 * | 5/1981 | |

Primary Examiner—Johann Richter
Assistant Examiner—Paul A. Zucker
(74) Attorney, Agent, or Firm—Renner, Kenner, Greive, Bobak, Taylor & Weber

(57) ABSTRACT

Disclosed is an integrated process for producing 2,6-naphthalene dicarboxylicacid comprising oxidizing a methylnaphthalene feedstock, hydrodebrominating the crude naphthoic acid product under conditions different from any work known in the art, forming a potassium salt of the acid; disproportionating the potassium salt to produce 2,6 potassium salts of NDA; selectively precipitating $K_2NDA$; selectively precipitating the monopotassium salt of 2,6 NDA (KHNDA); disproportionating the KHNDA into 2,6 NDA and K2NDA; further reacting the 2,6 NDA in a pipe reactor; and drying the product 2,6 NDA by conventional means or directly slurrying directly into a PEN process. The process can tolerate impurities in the economical methylnaphthalene feed and the resulting 2,6 NDA is of high quality with <50 ppm potassium.

56 Claims, 4 Drawing Sheets

U.S. PATENT DOCUMENTS

| | | | |
|---|---|---|---|
| 5,262,560 A | * 11/1993 | Holzhauer et al. | |
| 5,284,552 A | 2/1994 | Suzuki et al. | 203/64 |
| 5,292,934 A | 3/1994 | Sikkenga et al. | 562/413 |
| 5,329,058 A | 7/1994 | Shimada et al. | 585/452 |
| 5,391,291 A | 2/1995 | Winquist et al. | 208/143 |
| 5,510,563 A | 4/1996 | Smith et al. | 585/812 |
| 5,522,905 A | 6/1996 | Krutzsch et al. | 208/161 |
| 5,770,764 A | 6/1998 | Zeitlin et al. | 562/412 |
| 5,840,968 A | 11/1998 | Lee et al. | 562/486 |
| 5,859,294 A | 1/1999 | Hashimato et al. | 562/486 |

* cited by examiner

INTEGRATED PROCESS FOR THE PRODUCTION OF 2, 6-NAPHTHALENE DICARBOXYLIC ACID

This application claims the benefit of U.S. Provisional Application No. 60/151,577, filed Aug. 30, 1999, the entire disclosure of which is hereby incorporated by reference.

CROSS REFERENCE

This application is related to U.S. Application Ser. Nos. 60/151,607, 60/151,498, 60/151,602,60/151,603, 60/151,529, 60/151,489, 60/151,604, 60/151,606, 60/151,589, 60/151,497, 60/151,590, and 60/151,578, filed of even date, and incorporated by reference herein.

FIELD OF THE INVENTION

This invention relates to an integrated process for the manufacture of polymer grade 2,6-naphthalene dicarboxylic acid (2,6-NDA). Moreover, the invention allows an economic route to 2,6-naphthalene dicarboxylic acid, the preferred monomer for the production of polyethylenenaphthalate (PEN), via relatively inexpensive feedstock comprising methylnaphthalene feedstock. Methylnaphthalene is found in substantial concentration in cracked light gas oil (CLGO) produced as a by-product of ethylene production when heavy gas oil is the feedstock to the ethylene production unit. Methylnaphthalene is also produced in petroleum refineries, both in the light gas oil produced in refinery catalytic cracking operations, and in the bottom fractions of reformate from catalytic reforming operations. Coal tar, such as that produced in the steel industry, also contains methylnaphthalene. Another source of methylnaphthalene is the heavy aromatic stream generated by the UOP-BP Cyclar® process that converts liquified petroleum gases to aromatics.

The process disclosed herein is unique in many respects. Of particular importance, the new process can operate using relatively impure methylnaphthalene feedstock with respect to organic hydrocarbon impurities, allows for debromination of the oxidation product in the liquid phase, and avoids the isolation of purified naphthoic acid. It also produces the preferred monomer, naphthalene dicarboxylic acid (NDA), rather than naphthalene dicarboxylate (NDC), and optionally allows linkage to a PEN process without isolation and drying of NDA crystals.

BACKGROUND OF THE INVENTION

Naphthalene dicarboxylic acids are useful as intermediates leading to various industrial chemicals, dyestuffs and the like. Polyesters prepared from 2,6 naphthalene dicarboxylic acid and ethylene glycol, such as polyethylenenaphthalate (PEN), have excellent heat resistance, gas barrier, and mechanical properties as compared with polyethylene terephthalate. Films, fibers and other shaped articles prepared from PEN display improved strength and thermal properties relative to other polyester materials. High strength fibers made from PEN can be used to make tire cords and films made from PEN are advantageously used to manufacture magnetic recording tape and components for electronic applications. In order to prepare high quality PEN it is desirable to use purified 2,6-naphthalene dicarboxylic acid.

Methods for producing 2,6 naphthalene dicarboxylic acid are known in the art. One method is the oxidation of an alkyl or acyl substituted aromatic compound to the corresponding aromatic carboxylic acid using a heavy metal catalyst in the liquid phase. For example, U.S. Pat. Nos. 2,833,816; 3,856,855; 3,870,754; 4,933,491; and 4,950,786 disclose such oxidation methods.

In U.S. Pat. No. 3,856,855 there is disclosed a process for the preparation of NDA which consists essentially of oxidizing dimethylnaphthalene with molecular oxygen at a temperature within the range of 100° C. to 160° C. under an oxygen partial pressure of from about 2 to 8 atm in acetic acid of an amount of at least 4 parts by wt. per part by wt of dimethylnaphthalene in the presence of a Co/Mn/Br catalyst.

More recently, U.S. Pat. No. 5,292,934 disclosed a method for preparing an aromatic carboxylic acid by oxidizing an aromatic compound having at least one oxidizable alkyl or acyl group with oxygen in the presence of a low molecular weight carboxylic acid solvent and a heavy metal at a temperature of about 250° F. to 450° F., heating the product to about 550° F., and recovering the carboxylic acid.

The primary disadvantage of the methods that involve direct oxidation to 2,6NDA, is that impurities are trapped in the 2,6NDA oxidation product which forms upon oxidation as a solid in the oxidation solvent. In order to remove these impurities to a sufficiently low level acceptable for polymerization, the 2,6NDA product must be purified via multiple steps. These steps typically involve esterification, so that the resulting end product is 2,6naphthalene dicarboxylate, an ester, rather than the preferred 2,6napthalene dicarboxylic acid. Another disadvantage is that the methods referenced above require expensive base feedstocks and subsequent difficult synthesis reactions in order to prepare the feed for the oxidation to crude 2,6NDA.

Alternatively, naphthalene monocarboxylic acid and naphthalene dicarboxylic acids other than 2,6-naphthalene dicarboxylic acid can be converted to 2,6-NDA using a disproportionation reaction in the case of the monocarboxylic acids or a rearrangement reaction in the case of other naphthalene dicarboxylic acids. Henkel and Cie first patented a reaction of naphthoic acid salts to 2,6NDA in the late 1950s. (See U.S. Pat. No. 2,823,231 and U.S. Pat. No. 2,849,482).

U.S. Pat. No. 2,823,231 discloses a method of producing naphthalene 2,6-dicarboxylic acid from a naphthalene-monocarboxylic acid which comprises converting said naphthalene-monocarboxylic acid into a corresponding mono-alkali metal salt, heating said mono-salt to a temperature above about 360° C. and below the temperature at which substantial decomposition of the starting material and reaction product takes place, in an inert atmosphere of carbon dioxide and nitrogen and converting the dialkali metal salt of naphthalene 2,6-dicarboxylic acid formed thereby into free naphthalene 2,6-dicarboxylic acid by acidification of said di-alkali metal salt with a strong mineral acid.

Other patents have claimed improvements in particular aspects of the rearrangement type of reaction. U.S. Pat. No. 4,820,868 claims improvements in yield of 2,6-naphthalene dicarboxylic acid for specific isomers subjected to a rearrangement reaction.

U.S. Pat. No. 3,766,258 claims an improvement in yield in a process for carboxylation of metallic salts of aromatic mono-, di-, or polycarboxylic acids in the presence of a metal halide catalyst and acid binding agent, the improvement consisting of using, in addition to a heavy metal catalyst, a basic metal carbonate comprising cupric carbonate or chromium carbonate.

U.S. Pat. No. 3,671,578 discloses a process for preparing 2,6-naphthalene dicarboxylic acid which enables the re-use of alkali in the alkali salt of the starting naphthalene carboxylic acid formed by the rearrangement reaction.

U.S. Pat. No. 3,952,052 discloses separation of metal salts of polycarboxylic acids by flash evaporation of the dispersant, where the dispersant is selected from biphenyl, terphenyl, quaterphenyl, and isomers and mixtures thereof.

U.S. Pat. No. 3,631,096 claims improvements in the yield of polycarboxylic acid salts by carrying out the transformation process in an inert atmosphere and in the presence of a transformation catalyst having present therewith as an adjuvant an ammonium salt of an aromatic acid.

There have been a number of references in the art which describe work relating to improved methods of purifying crude 2,6-naphthalene dicarboxylic acid. U.S. Pat. No. 3,888,921 provides a method for purifying a crude 2,6 NDA by preparing a dialkali salt, precipitating 40 to 97 mol %. of the dialkali 2,6 NDA as a monoalkali salt, and converting the precipitate to 2,6NDA.

The production of terephthalic acid provides additional relevant information regarding the art in this field. For example, U.S. Pat. No. 4,430,511 discloses an improvement in a method of producing terephthalic acid which comprises forming aggregates of crystals by direct precipitation and mixing the crystals with terphenyl to form a low viscosity slurry and transporting the slurry to a disproportionation reactor.

In the art relating to producing terephthalic acid it is also known to remove contaminants from the catalyst used in the process. For example, in U.S. Pat. No. 4,263,451, carbon impurities are removed from Zno & oxides of carbon by passing the effluent through a filter which collects the oxides of carbon.

U.S. Pat. No. 2,927,130 provides a method of recovering terephthalic acid from an aqueous solution containing alkali salts of terephthalates.

Canadian Patent 864587 discloses a process for the preparation of 2,6-NDA which comprises heating a monoalkali salt of 2,6-NDA in water or water-containing organic solvent causing disproportionation thereof into 2,6-NDA and dialkali salt and separating the 2,6-NDA.

In uk 1 472 777 it is claimed that the surface area of 2,6-NDA crystals is critical in producing pen with superior properties, including high softening point and improved color, and a method is provided for producing the specific crystals.

Currently, the most common process for making 2,6NDA starts with relatively expensive o-xylene and butadiene feedstocks, as discussed, for example, in U.S. Pat. No. 5,510,563 and U.S. Pat. No. 5,329,058 and incurs substantial yield losses of these starting materials. Following the synthesis and purification of 2,6dimethylnaphthalene (2,6 DMN), 2,6 DMN is oxidized to produce crude NDA product which forms as a solid with impurities trapped within. Therefore, in such processes, esterification to naphthalene dicarboxylate (NDC) is necessary to eliminate the impurities, as discussed in U.S. Pat. Nos. 5,254,719 and 4,886,901. Direct purification of the crude NDA via hydrogenation has been suggested by U.S. Pat. No. 5,292,934, but requires a difficult and expensive high temperature hydrogenation in the presence of a solvent. Another proposed purification scheme requires the use of nitrogen- containing species. (See U.S. Pat. No. 5,770,764 and U.S. Pat. No. 5,859,294). Crystal size and morphology is important in either case, whereas the novel process disclosed herein can optionally avoid the issue of controlling particle size of the final product.

Currently NDC is commercially available, but NDA is not, presumably because of the difficulty of producing polymerization grade NDA without esterifying to NDC. Ideally, if NDA were available commercially at a competitive price, NDA would be preferred over NDC as the starting monomer for PEN. Alternative routes to NDA based on the rearrangement reaction have been plagued with difficulties associated with handling solids, the inefficient recycling of potassium, and ineffective integration from feedstock through final product. Although various improvements have been suggested over the years, there is still a distinct need in the art for an economical, integrated process for producing 2,6-NDA, the preferred monomer for the production of polyethylenenaphthalate (PEN).

SUMMARY

In accordance with the foregoing, the present invention is an integrated process for producing 2,6-naphthalene dicarboxylic acid, which comprises:

a) Reacting a hydrocarbon stream containing predominantly methylnaphthalene with an oxygen-containing gas in the presence of a suitable solvent and catalyst to form a crude mixture of naphthoic acid (crude product NA), wherein said crude product NA remains dissolved in the solvent;

b) Recovering said crude product NA by evaporation of solvent and washing said crude product NA with water;

c) Debrominating said crude product NA by passing over a supported catalyst in the presence of hydrogen, and water-washing said crude debrominated product NA;

d) Contacting said crude, debrominated product NA with an aqueous base of potassium to extract pure NA as the aqueous potassium salt of NA;

e) Separating said aqueous potassium salt of NA from the remaining organic liquid (containing methylnaphthalene and partially oxidized reaction intermediates), and recycling said organic liquid to step a);

f) Contacting said aqueous potassium salt of NA with naphthalene vapor, adding a solid catalyst, and removing water by evaporation to form a slurry of solid potassium salt of NA and catalyst suspended in liquid naphthalene;

g) Reacting said slurry in the presence of carbon dioxide to convert solid potassium salt of NA to liquid naphthalene and solid dipotassium salt of 2,6-NDA(2,6-K2NDA);

h) Reducing the pressure to vaporize the naphthalene, and separating the solids from the naphthalene vapor by a novel separation using cyclones, recycling a portion of the naphthalene to step (f), and recovering the remainder as a product, or methylating the naphthalene via direct alkylation or transalkylation to provide additional methylnaphthalene feed for step (a);

i) Contacting the solids with water to create a mixture of aqueous potassium salts (comprising the potassium salt of NA, KNA, and the dipotassium salt of 2,6-NDA, 2,6-K2NDA, and its isomers) and solid catalyst;

j) Separating the solid catalyst from the mixture of aqueous potassium salts and recycling it to step (f);

k) Adding aqueous potassium bicarbonate to the mixture of aqueous potassium salts and evaporating a portion of the water to selectively crystallize the dipotassium salt of 2,6-NDA as a solid, separating said solid, and recycling the remaining liquid to step (d);

l) Dissolving the solid dipotassium salt of 2,6-NDA in water;

m) Optionally passing said aqueous dipotassium salt of 2,6-NDA through an activated carbon bed to remove impurities;

n) Contacting said aqueous dipotassium salt of 2,6-NDA with carbon dioxide to create a mixture of solid monopotassium salt of 2,6-NDA and aqueous potassium bicarbonate, separating said solids, and recycling the aqueous potassium bicarbonate to step (k);

o) Contacting solid monopotassium salt of 2,6-NDA with water, optionally in the presence of carbon dioxide, to form solid 2,6-NDA, aqueous dipotassium salt of 2,6-NDA, and potassium bicarbonate;

p) Separating the solid 2,6-NDA and recycling the liquid containing aqueous dipotassium salt of 2,6-NDA and potassium bicarbonate to step (n);

q) Contacting solid 2,6-NDA with water in a pipe reactor to remove traces of potassium ion impurity;

r) Separating solid 2,6-NDA and recycling water to step o);

s) Washing the solid 2,6NDA with additional water t) Separating the water from the solid, producing wet polymer grade 2,6NDA, and recycling most of the water to step q)

u) Drying solid 2,6-NDA by conventional means, or optionally feeding as an aqueous slurry to a process for making PEN, optionally adding additional water if necessary.

The integrated process produces the preferred 2,6-NDA isomer, and demonstrates many novel steps and advantages over any process available in the art.

DETAILED DESCRIPTION OF THE INVENTION

The present invention offers a very efficient integrated process for producing the preferred 2,6 NDA from inexpensive olefin plant and refinery feedstock and demonstrates a number of novel aspects and advantages over any process available in the art. One skilled in the art will recognize that the process could easily be adapted to utilize methynaphthalene from other sources as well. The process allows oxidation of crude methylnaphthalene feed, and includes improved oxidation product purification steps, including a novel hydrodebromination step, and eliminates the need to isolate a pure acid intermediate. The present invention incorporates a disproportionation step, followed by new steps in separation and purification of the disproportionation product, and also demonstrates very efficient potassium recycle. Optionally, the process allows for efficient recycle of the reaction co-product and conversion into additional methylnaphthalene feed.

Elimination of the product drying step is also a novel option with the current process, thus eliminating concerns regarding final product crystal size and morphology.

Figure 1:
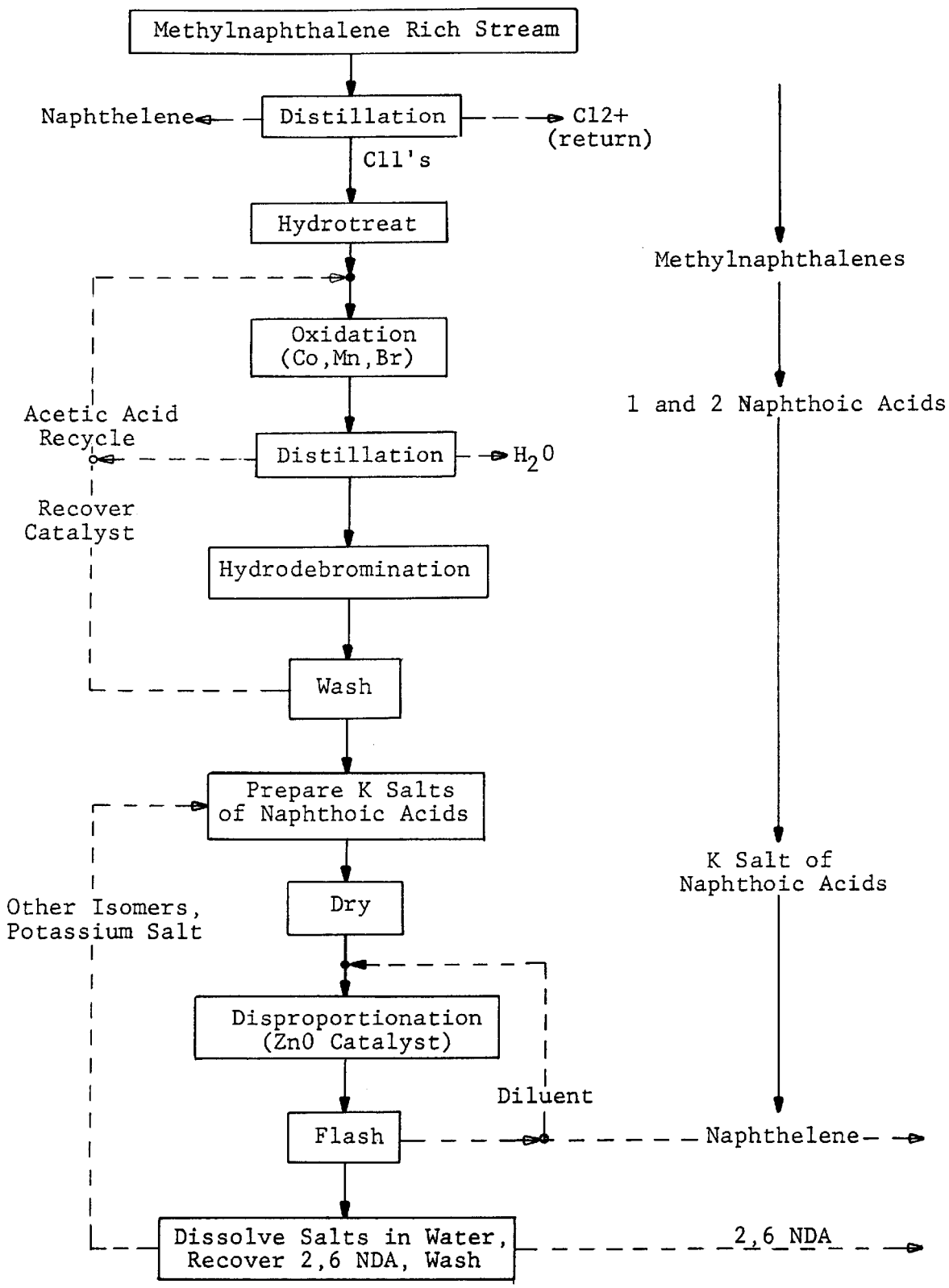
FIG. 1 is a block flow chart showing the steps of the preferred embodiment of the present invention.

An overview of the key steps of the integrated process is shown in FIG. 1. CLGO which has been hydrotreated to remove sulfur is distilled into three fractions comprising:

a. crude napthalene b. crude methylnaphthalene c. dimethylnaphthalene+heavier compounds.

Alternatively, the distillation could be performed first, with only the crude distilled methylnaphthalene fraction being passed through the hydrotreater. The choice of hydrotreater position depends on the economics of the process, and in particular, whether or not there is a market for very low sulfur naphthalene and dimethylnaphthalene fractions.

The methylnapthalene fraction is fed into an oxidation reactor. For most commercial feedstock sources, the methylnaphthalene will be a mixture of two isomers, 1-methylnaphthalene and 2-methylnaphthalene. The methylnaphthalene is oxidized to a mixture of the corresponding isomers of naphthoic acid in the presence of a catalyst comprising Co, Mn and Br. The resulting crude product naphthoic acid remains in the liquid phase. The mixture of isomers of napthoic acid are recovered by an evaporative distillation which removes acetic acid, and subsequently washed with water to remove inorganic Br, phthalic acid, trimellitic acid and Co/Mn. The crude product NA is hydrodebrominated by passing the crude product NA over a catalyst comprising palladium on carbon, the debromination taking place in the absence of solvents. The debrominated crude product NA is then washed again with water to remove residual inorganic bromine.

The crude, debrominated naphthoic acid is reacted with basic potassium in 0–50% molar excess at a temperature of about 100° C. to form a concentrated solution of the dipotassium salt of the acid and to drive off carbon dioxide. The dipotassium salt of naphthoic acid and said by-products are separated. The naphthalene by-products are recycled back to the oxidation reactor. Water is added to the dipotassium salt of naphthoic acid and the aqueous solution is pumped into a reactor where water is evaporated.

The aqueous solution is then contacted with hot napthalene and the aqueous solution of salts and naphthalene is introduced into a reactor as a slurry to which has been added a catalyst comprising ZnO in an amount of about 5–20% by weight.

The naphthalene slurry containing particulate salts and ZnO catalyst is reacted in a disproportionation reactor to produce 2,6-K2NDA. The disproportionation step is optionally, and preferably, repeated in a second disproportionation reactor to improve yields.

After disproportionation the napthalene is flashed from the reaction product. The flashed naphthalene is heated and recycled for use in the evaporation of water from potassium salt, and for use as a diluent for potassium The liquid carrying mixed organic salts is introduced into a two-stage evaporative crystallization section where the K2NDA is selectively precipitated, the $KHCO_3$ is recycled, and the purified K2NDA is redissolved with additional $H_2O$. Then, the purified K2NDA is passed through an activated carbon bed.

Next, the monopotassium salt of 2,6-NDA, (KHNDA) is selectively precipitated and the KHNDA solids are disproportionated into 2,6-NDA and K2NDA. The product of disproportiona-tion is centrifuged to yield a 2,6NDA slurry, and a centrate containing predominantly 2,6K2NDA and $KHCO_3$. Residual potassium is removed by passing the 2,6NDA through a pipe reactor and washing the 2,6-NDA in water at about 150° C. Finally, the 2,6-NDA is dried by conventional means or directly slurried into a process for producing PEN.

As will be apparent to those skilled in the art from the more detailed discussion, which follows, the integrated process demonstrates a number of improvements over the prior art and any currently available process for making 2,6-NDA.

Figure 2:
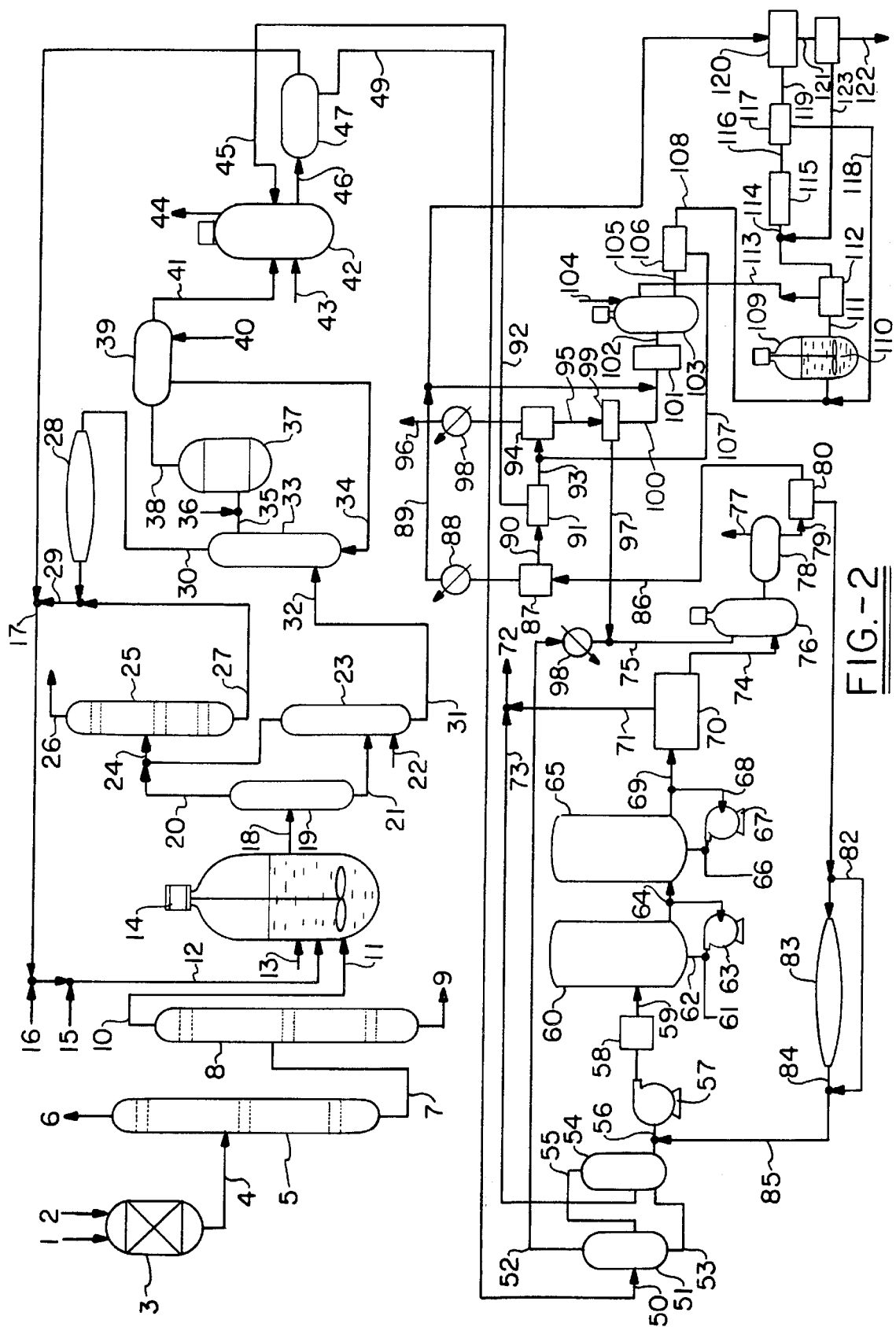
FIG. 2 is a process flow diagram illustrating a preferred embodiment of producing 2,6-NDA according to the process of this invention.

FIG. 2 shows in more detail in schematic form the preferred embodiment for operating the process of this invention. The methylnaphthalene-containing stream 2 is fed into a hydrotreater 3 to remove sulfur and nitrogen along with hydrogen which is fed in at 1. The conditions in the hydrotreater 3 are about 250 psi and 400° C.

The desulfurized crude methylnaphthalene containing stream 4 enters a first distillation column 5 where crude naphthalene is taken off the top 6 and C11 and C12 naphthalenes and heavies exit the bottom 7 and enter a second distillation column 8. In the second distillation column 8, C12 and heavier fractions exit the bottom, at 9, and can be used in solvents or blended as fuel. The desired methylnaphthalene is approximately 80–95% pure and is taken off the top of the column at 10.

A stream of 80–95% methylnaphthalene represented by 11 enters an oxidation reactor 14. Also entering the oxidation reactor 14 is a stream represented by 12 containing recycled acetic acid from 27, acetic acid make-up which enters at 15, fresh Co/Mn/Br catalyst which enters at 16, and recycled catalyst from a means for catalyst recovery and regeneration, 28. In practice, the streams represented by stream 12 may enter the reactor individually. A compressed oxygen-containing gas for the oxidation reaction is supplied at 13. Conditions in the oxidation reactor 14 are moderate, for example about 150° C. and 300 psi is acceptable. The primary products of the oxidation reaction are naphthoic acid and water. Both isomers of naphthoic acid are produced, 1-naphthoic acid and 2-naphthoic acid, the relative ratio being determined approximately by the relative ratio of 1-methylnaphthalene to 2-methylnaphthalene in the oxidation feed. Minor amounts of trimellitic acid, phthalic acid, other organic compounds, and carbon dioxide are also formed in the reactor, and some methylnaphthalene remains unreacted. The reactor effluent 18 exits the oxidation reactor 14 and enters a distillation column 19 which separates acetic acid and water off the top, represented by 20, and recovers the crude naphthoic acid oxidation product which exits the bottom 21. The crude naphthoic acid oxidation product 21 enters a steam stripping column 23 where steam is supplied at 22. Additional acetic acid and water are taken off the top of 23, and combined with stream 20 to create stream 24. Stream 24 is routed to a distillation column 25, where waste water exits the top 26, and recovered acetic acid 27 exits the bottom and is recycled to the combined oxidation feed stream 12.

The crude naphthoic acid, as a liquid, exits column 23 at 31, at a temperature above its melting point which is about 150° C. The crude naphthoic acid product 32, then flows countercurrent to an aqueous wash stream through a first aqueous extraction 33, a hydrodebromination step 37, and a second aqueous extraction step 39. The crude naphthoic acid product first enters aqueous extraction step 33. This extraction step effectively removes inorganic bromine, by-product phthalic acid, trimellitic acid, and much of the cobalt and manganese, all of which exit the wash at 30, and are recycled to a means for catalyst recovery and regeneration, represented by 28, which is prior to the point for reentry of the recycled acetic acid 29. The water used in the first aqueousi extraction step 34, is recycled water which has been cascaded into 33 from the second aqueous extraction 39. After the aqueous extraction in 33, the crude naphthoic acid product is directed, along with added hydrogen 36, to a hydrodebromination reactor 37 where the crude product is debrominated in the absence of solvent, of a Pd on carbon catalyst at a temperature of about 220° C. and 100 Psi $H_2$ to eliminate any brominated organic products formed in the oxidation. The absence of solvent distinguishes the debromination from other work in the field. Eiting crude naphthoic acid product 38 then enters a second aqueous extraction 39 where it is washed with water to remove residual inorganic bromine compounds created during the hydrodebromination reaction. Fresh water is added at 40.

The washed debrominated crude naphthoic acid product 41 is routed to the salt formation reactor 42 where the potassium salt of naphthoic acid is formed. Make-up potassium stream 43 is also added to the salt formation reactor 42, as needed, to maintain the desired potassium ratio of 0–50% molar excess. The primary source of potassium to the reactor is recycled potassium bicarbonate contained in stream 45, which originates in a later section of the process. Stream 45 also contains KNA, the dipotassium salt of 2,3 NDA, and low levels of the potassium salt of 2,6-NDA, in addition to the recycled potassium bicarbonate. In the salt formation reactor 42 streams 41, 43, and 45 react to form a concentrated solution of the potassium salt of the naphthoic acid. In order to drive the equilibrium reaction, $CO_2$ is driven off at 44 by heating to about 100° C. The crude potassium salt of naphthoic acid product is directed to a phase separator 47 where the potassium salt in water 49 is channeled toward the disproportionation section of the process and the remaining organic phase residual 48, containing unreacted methylnaphthalene, naphthaldehydes, and other minor components, is recycled back to the oxidation section. It is expected that with recycle the oxidation yield to naphthoic acids should be in excess of 90%, based on extrapolation of experimental data.

The aqueous solution 49 containing the potassium salt of naphthoic acid, along with other compounds resulting from recycled stream 45, enters a two-stage countercurrent water removal system, 51 and 54, at 50. Regenerated ZnO catalyst and make-up ZnO catalyst enter 51 and 54 by way of line 85. Water is evaporated from the combined feed stream 49 with hot recycled naphthalene 73, cascaded back through 54 and 51. Line 52 exits the first stage water removal step 51 containing steam and about 25% naphthalene. The water concentration of the combined disproportionation feed exiting 54 should be reduced to less than 1000 ppm, to assure optimal disproportionation yields, and to avoid significant decarboxylation of the disproportionation reaction product.

The naphthalene slurry exiting 54, containing the solid particulate salts and 5–20% by weight ZnO catalyst, is fed via pump 57 through furnace 58 to the first disproportionation reactor 60 at about 450° C. and 850 psi. Make-up $CO_2$ is fed through stream 61 to maintain the total pressure. In reactor 60 potassium naphthoate (KNA) disproportionates to the dipotassium salt of NDA and naphthalene. The NDA formed is predominantly 2,6-NDA, with minor amounts of 2,3-NDA. The second stage reactor 65 helps to increase conversion. Another stream of make-up $CO_2$ is fed through stream 66 to maintain the total pressure. Mixing is accomplished via circulation pumps 63 and 67. The disproportionation reactor solids exit 65 in line 69 as a slurry in naphthalene, and consists of 2,6K2DNA, 2,3 K2NDA, unreacted KNA, catalyst, and trace coke. The slurry 69 then enters a means for pressure letdown and flashing naphthalene 70.

The effluent slurry 69 with solids in liquid naphthalene then enters a product separation section 70 with a means for pressure letdown and flashing all liquid naphthalene and dissolved $CO_2$ into vapor. Within 70, following pressure letdown, are included a series of cyclone separators to separate out solids from naphthalene vapor. Additional details of Section 70 are included in FIG. 3, discussed below. Naphthalene and $CO_2$ vapor from product separation section 70 exit by stream 71. The net naphthalene produced by the disproportionation reactors 60 and 65 is taken out of naphthalene vapor steam, represented by 71, through stream 72 and is either condensed for production of additional methylnaphthalene via transalkylation with dimethylnaphthalene (FIG. 4) or sold to the merchant market. The remaining naphthalene and $CO_2$ vapor steam 73 is recycled to vaporize water in the two-stage water removal system 51 and 54, as discussed above, and the recycled naphthalene vapor is condensed and reused as a carrier and diluent for the disproportionation reactor feed stream 59.

Figure 3:
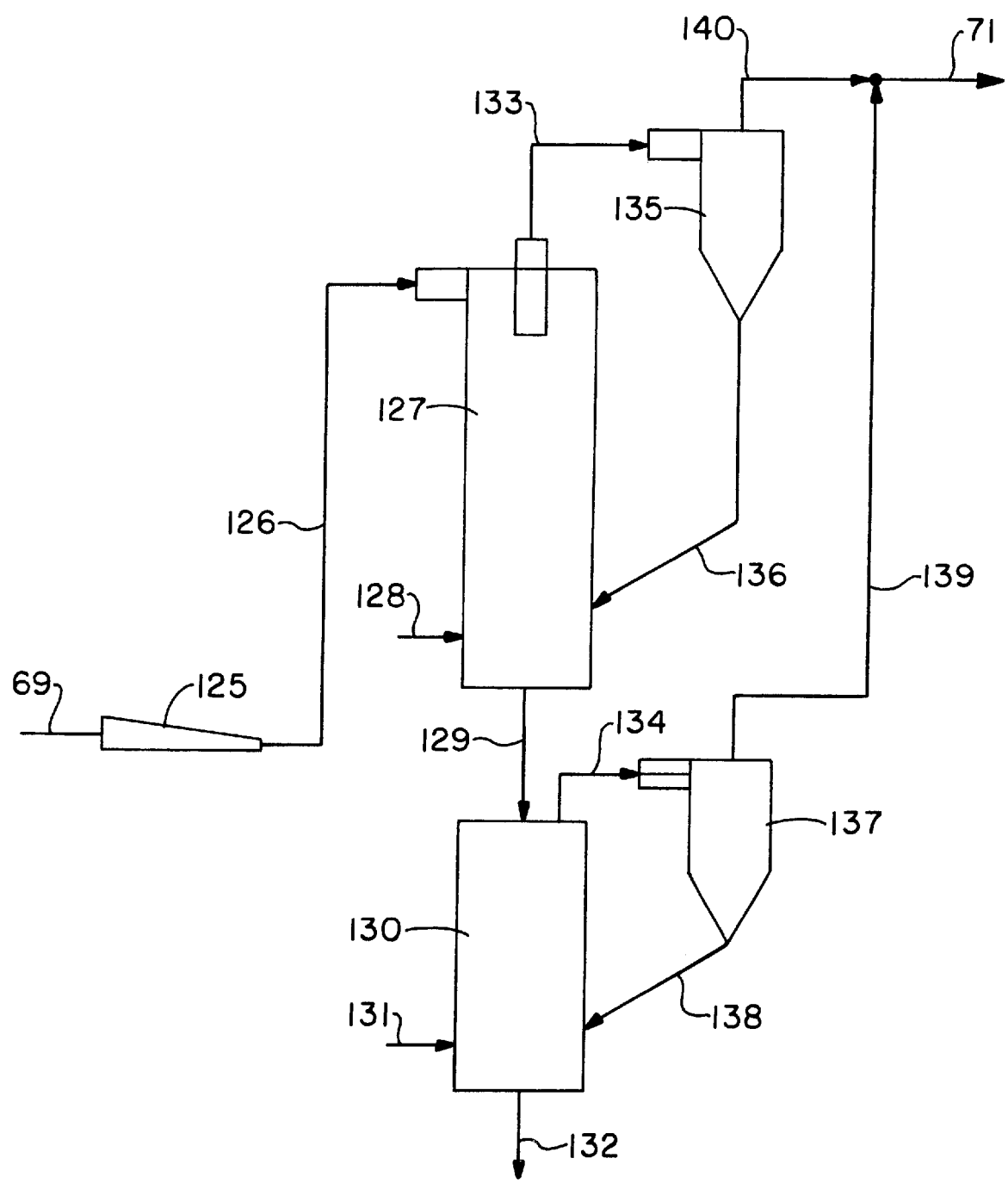
FIG. 3 is a process flow diagram illustrating in further detail the means for pressure letdown and cyclone separators, 70, of FIG. 2.

The pressure letdown section and cyclones of 70 of FIG. 2 are shown in more detail in FIG. 3. In FIG. 3, the effluent slurry 69 enters tapered bore section 125 where pressure is let down, leading to flashing of all liquid naphthalene and $CO_2$ in 69, thus converting 69 from a liquid/solid slurry to a gas/solid mixture in 126. The mixture in 126 first enters a stripper cyclone 127 where most of solids in the gas/solid mixture are separated and kept in the lower part of 127 for stripping. Naphthalene and $CO_2$ vapor with some entrained solids then exit at 133 and enter a second stage cyclone 135. Additional solids are separated in 135 and returned to the lower part of the stripper cyclone 127 via 136 for stripping. Naphthalene and $CO_2$ vapor exit 135 at 140. The solids in the lower part of 127 are stripped with $CO_2$ via 128. The stripped solids 129 exit 127 and enter the second stage stripper 130 where additional $CO_2$ is introduced via 131. The stripping gas and entrained solids exit at 134 and enter cyclone 137 where most solids are separated and returned to stripper 130 via 138. The stripped K2NDA solids exit at 132 which correlates with FIG. 2 at 74. The stripping gas exits 137 at 139 which combines with 140 to become the recycle naphthalene and $CO_2$ stream 71, as discussed in the description of FIG. 2.

Again referring to FIG. 2, following the pressure letdown section 70, the solid product comprising dipotassium salts of NDA, K2NDA (2,6 and 2,3 isomers), unreacted KNA, catalyst, heavy by-products, and trace coke exit by pathway 74 and enter water wash 76 where the organic salts are dissolved. Steam and 25% naphthalene from 52 can enter the water wash via 75. The liquid is then directed to a phase separation vessel 78 to separate the naphthalene phase from the aqueous phase. Naphthalene and some solids exit the process at 77, while crude K2NDA and most of the ZnO catalyst are directed to a centrifuge 80 via transfer line 79. ZnO catalyst exits the centrifuge through 81 and is recycled. The liquid carrying the mixed organic salts, including the crude K2NDA is directed through 86 to an optional filter which not shown, and then to a two-stage evaporative crystallization section, 87 and 94.

In the evaporative crystallization section 2,6-K2NDA is selectively precipitated from crude K2NDA product, rejecting KNA, 2,3-K2NDA, and $KHCO_3$. First, the crude K2NDA stream 86 and a recycle stream 97 containing $KHCO_3$ are added to evaporative crystallizer 87. The crude NDA solution concentration is approximately 20 wt %. In evaporative crystallizer 87, 2,6-K2NDA is selectively precipitated as water is evaporated. The water vapor exits the crystallizer, and is condensed by overhead exchanger 88. The water is then routed through line 89 to other portions of the finishing section in order to provide a dilution medium. The contents of the first evaporative crystallizer 87 exit through 90 to centrifuge 91. In centrifuge 91, mother liquor containing KNA, 2,3-K2NDA, and $KHCO_3$ are rejected, exit at 92, and are recycled back to the salt formation reactor 42 through 45. The K2NDA solids are combined with recycle stream 107 containing $KHCO_3$ and 2,6-K2NDA and added to the second stage evaporative crystallizer 94. In 94 2,6-K2NDA is again selectively precipitated as water evaporates and exits the crystallizer. The water is condensed by overhead exchanger 96 and is directed into line 89. The purified K2NDA slurry leaves the second stage evaporative crystallizer through 95 and directed to centrifuge 99. In centrifuge 99 mother liquor containing $KHCO_3$ is separated from purified 2,6-K2NDA and recycled back to the first stage evaporative crystallizer 87 through 97, or optionally recycled to stream 75. At this point the 2,6-K2NDA organic purity should be greater than 99.9%.

The purified solid 2,6-K2NDA is dissolved with water from overhead line 89 to make an approximately 20 wt % aqueous solution and transported through line 100 to an activated carbon guard bed 101. The 20 wt % 2,6-K2NDA solution then passes through the activated carbon guard bed 101 to remove residual trace impurities that could affect the color of the final product.

The approximately 20 wt % 2,6-K2NDA solution exits the activated carbon bed 101 via line 102 and is directed to the $CO_2$ precipitation reactor 103. $CO_2$ is added to reactor 103 through line 104. In reactor 103 the monopotassium salt of 2,6-NDA, KHNDA, is selectively precipitated from the approximately 20 wt % 2,6-K2NDA solution. Yields of 80%+ have been demonstrated at only 1 ATM $CO_2$ pressure. The KHNDA is then directed out of the reactor through line 105 to centrifuge 106. The mother liquor, containing $KHCO_3$ and unreacted 2,6-K2NDA, is separated from the solid KHNDA and is recycled back to the second stage evaporative crystallizer 94 via line 107. The solid KHNDA is slurried to approximately 5 to 10 wt % with water from recycle line 118 and directed through line 108 to disproportionation reactor 109. $CO_2$ is added to reactor 109 through line 110. The KHNDA is reacted in the presence of 50 psig $CO_2$ and about 150° C. in disproportionation reactor 109 to form solid 2,6-NDA and 2,6-K2NDA. The reactor effluent from this step is directed through 111 to centrifuge 112. In centrifuge 112, the solid 2,6-NDA is separated from the mother liquor. The centrate containing predominantly 2,6-K2NDA and KHNDA is directed through 113 and recycled back to the $CO_2$ precipitation reactor 103. The solid 2,6-NDA is slurried with recycle water from line 123 in approximately a 1 to 5 weight ratio, respectively, and directed through 114 into a pipeline reactor 115. In the pipeline reactor 115 the slurry is reacted at approximately 150° C. for 30 to 60 minutes under plug flow conditions in order to drive the KHNDA disproportionation reaction toward completion and to remove trace potassium. The pipeline reactor contents exit through line 116 and are directed to centrifuge 117. In centrifuge 117 water and other trace contaminants are removed from the 2,6-NDA solid and recycled back to line 108 and to disproportionation reactor 109. The 2,6-NDA solid exits at 119, is then combined with water from line 89, and is then hot water washed in vessel 120 at approximately 150° C. with approximately a 5 fold of excess water. The slurry exits 120 through line 121 to centrifuge 122. In centrifuge 122, the pure 2,6-NDA solid is separated from the water. The centrate is recycled back to line 114 and the pipeline reactor 115 through line 123. At this point in the process potassium levels should be well below 50 ppmw in the 2,6-NDA solid. The 2,6-NDA solid then can be dried by conventional methods or directly slurried to a PEN process.

Following is a more detailed discussion of the features of the integrated process:

Inexpensive Feedstock

One of the many advantages of the integrated process is that the oxidation step can tolerate crude methylnaphthalene feed, due to a novel post-oxidation purification train that produces a bromine free solution of the potassium salts of 1- and 2-naphthoic acid. Oxidation steps in other processes to produce polymer grade monomers require relatively pure feed to the oxidation train. The only commercial process currently used in the art uses o-xylene and butadiene as feedstock. In contrast, the only requirement for the feedstock for the present invention is that it contains large quantities of methylnaphthalenes. Sources could therefore include cracked light gas oils (CLGO) from an olefin plant, catalytically cracked light gas oils (CLGO) and other suitable fractions from refinery catalytic cracking units.

The preferred feedstock for use in the present invention is cracked light gas oil, which is often produced in significant quantities when heavy gas oil is fed to an ethylene production unit. The CLGO is rich in naphthalene, methylnaphthalene, di-alkylnaphthalenes, tri-alkylnaphthalenes, tetra-alkylnaphthalenes and other di-ring aromatics. Typically, CLGO from a heavy gas oil olefin plant contains in the range of 50–80% naphthalene(s) by volume, while CLGO obtained from a refinery catalytic cracker typically contains 5–35% naphthalene(s).

Other sources of methylnaphthalene can include heavy reformate from a catalytic reformer and the bottoms of BTX and plants which process heavy naphtha. These streams contain very low levels of heteroatoms and therefore require less hydrotreating. As noted above, another source of methyl naphthalene is the Cyclar® process, discussed in *Handbook of Petroleum Refining Processes*, Meyers, Robert A. (Ed.), R. R. Donnelly, 1986, Ch.2.

Hydrotreating

It is desirable to subject the feedstock to mild hydrotreating to remove sulfur and nitrogen. The C11 feedstock used in the present invention typically initially contained about 100 ppm nitrogen and about 350 ppm sulfur. An alternative source typically contained about 1600 ppm sulfur and a slightly lower amount of nitrogen initially. Other possible streams from which naphthalene could be extracted, such as, for example, feed from a catalytic cracker would typically have even higher levels of sulfur. In the case of feedstock from a cat cracker, it would not be unusual to have 1% sulfur. It is desirable to reduce sulfur to less than 50 ppm, preferably less than 10 ppm, and most preferably below 5 ppm.

The hydrotreating can take place before or after distillation. All of the CLGO feedstock can be hydrotreated before distillation; or hydrotreating can take place after distillation on C10 to C12 compounds, or more specifically on the methylnaphthalene fraction. In FIG. 1 and FIG. 2, CLGO is shown as being first hydrotreated, then distilled.

The hydrotreater location should be optimized based on the specific plant design and disposition of each fraction. Positioning the hydrotreater first in the process has the advantage of producing a higher quality naphthalene stream, at nominal net additional cost. Hydrotreating the full stream also allows downstream distillation and recovery of a low sulfur, low nitrogen, dimethylnaphthalene fraction. The resulting dimethylnaphthalene fraction could be used for transalkylation with naphthalene to produce additional oxidation feedstock, as will be discussed below, or sold as an aromatic solvent.

A suitable catalyst for use in hydrotreating is selected from Group VIII and/or VIB of the Periodic Table. Preferred metals include nickel, cobalt, molybdenum, and tungsten. Examples include catalysts selected from Ni/Mo, Ni/W, and Co/Mo, optionally on a support.

In the preferred embodiment, good results were achieved using C-448, 1.3 mm trilobe which was sulfided before use. C-448 is a catalyst commercially available from Criterion Catalyst Co. containing cobalt and molybdenum on an aluminum support. When used under the conditions outlined herein, C-448 offers an attractive combination of high desulfurization activity with low naphthalenes() hydrogenation activity.

Where the catalyst is on a support, the support may be selected from Groups II, III, IV, or V of the Periodic Table. The preferred supports include magnesia, alumina, silica, zirconia, zeolites such as zeolite Y and titania, as well as mixtures thereof. The preferred support is alumina.

The catalyst may also be a bulk-metal catalyst prepared through coprecipitation of the different metal salts. The nickel or cobalt bulk-metal catalysts may also contain other metals, particularly molybdenum. Said catalysts may be employed in many forms, including tablets, extrudates, powders, etc.

The conditions for hydrotreating in this process may be different from those generally selected for conventional hydrotreating where conditions might include more elevated hydrogen pressure and lower temperatures. Here suitable conditions for the process of the invention will be selected to eliminate the heteroatoms, but avoid hydrogenation of the naphthalene(s) as much as possible. The temperature will be somewhat higher and the pressure somewhat lower than used in conventional hydrotreating of refinery streams. A suitable pressure for hydrotreating in the present invention is from about 200 psig to 700 psig. The preferred range is from about 250 psig to 500 psig, and the most preferred is from about 200 to 350 psig.

A suitable temperature for hydrotreating the CLGO stream is from about 150° C. to about 600° C. A preferred range is from about 200° to 500° C., and the most preferred is from about 350° C. to 425° C.

The molar hydrogen to oil ratio used can range from 0.5:1 to 50:1. The preferred molar hydrogen to oil ratio is about 10:1.

The WHSV for hydrotreating the CLGO stream may be from about 0.5 to 6 per hour. The preferred WHSV is impacted by the temperature and pressure used and the heteroatom level in the starting feedstock. Higher WHSV can be used if the feedstock contains low levels of hydrotreatable heteroatom species and if the hydrotreating is conducted at higher temperature and hydrogen partial pressure.

In some situations it may be advantageous to hydrotreat after distillation. In several respects this might be easier, because there is not as much sulfur to remove since less of the heavier fractions remain, the boiling range of the feedstock is narrower, and not as much hydrogen would be required. This would be a capital advantage. Another advantage would be that a smaller hydrotreater should be adequate. The required conditions would be in the same ranges as discussed above.

An advantage in hydrotreating before distillation is that the hydrodesulfurization of the whole material allows some molecules in fractions above and below the desired methylnaphthalene fraction to contribute by cracking to the total amount of methylnaphthalene.

Distillation

As shown in FIG. 1, CLGO is first hydrotreated, then distilled into three primary fractions: 1) crude naphthalene; 2) crude methylnaphthalene (2 isomers); and 3) dimethylnaphthalene+heavier compounds.

The cracked light gas oil typically contains about 50 to 80%, C10 to C12 naphthalene(s) which may yield between 20 to 45%, but most often about 25–35% methylnaphthalene after distillation.

The boiling range of the CLGO used as the crude feedstock is from about 350° F. to about 650° F. The boiling range of the fraction containing the most methylnaphthalene is from about 435°–475° F. The lighter fractions of the CLGO tend to have lower amounts of sulfur, whereas the heavier fractions have much higher levels of sulfur. After hydrotreating the CLGO at 400° F., 250 psig, a molar hydrogen to oil ratio of 10:1 and WHSV=4 hr$^{-1}$ the level of sulfur in the fraction boiling between 435°–455° F. was 4 ppm while the level of sulfur in the fraction boiling between 455°–475° F. was 7 ppm. The nitrogen level in these two fractions was 32 and 35 ppm respectively. The higher boiling fractions contained higher levels of sulfur and nitrogen.

The distillation was conducted in a 1 gallon kettle equipped with an 1 inch Oldershaw column packed with Propack material to improve the separation efficiency of the column. The distillation was conducted with a reflux ratio of 5:1 at a pressure of 80 torr. The reported boiling points of the collected fractions were corrected for pressure and reported as boiling at 760 torr.

The methylnaphthalene fraction recovered via distillation may in some cases require further purification to remove the residual heteroatom impurities, (mainly nitrogen species) via an azeoptropic distillation with ethylene glycol, although this step is avoided in the preferred embodiment. The azeotropic distillation procedure mentioned in U.S. Pat. No. 5,284,552 can reduce the level of the sulfur and nitrogen in the hydrotreated fraction boiling between 455–475° F. to 3 ppm sulfur and 4 ppm nitrogen. In the present invention, the product of the feed purification section is a mixture of 1-and 2-methylnaphthalene, which is fed to an oxidation reactor. A key advantage of the process design is that the oxidation can tolerate impure feeds, and does not require a purity greater than about 85 to 90% methylnaphthalenes.

Optional Alkylation to Provide Additional Methylnaphthalene Feed

The CLGO feedstock used in the integrated process of this invention is unique in that distillation of it provides 20–35% methylnaphthalene. It is possible to obtain additional methylnaphthalene by alkylating naphthalene with additional multi-branched, mono- or di-aromatics from fractions on either side of the methylnaphthalene. Alkylating agents such as, but not limited to, mixed xylenes, dimethylnaphthalene, or methanol can be used at an elevated temperature and pressure and at a WHSV of about 3–8/hr over an alkylating catalyst, such as, for example, a zeolite such as zeolite Y or Beta.

Figure 4:
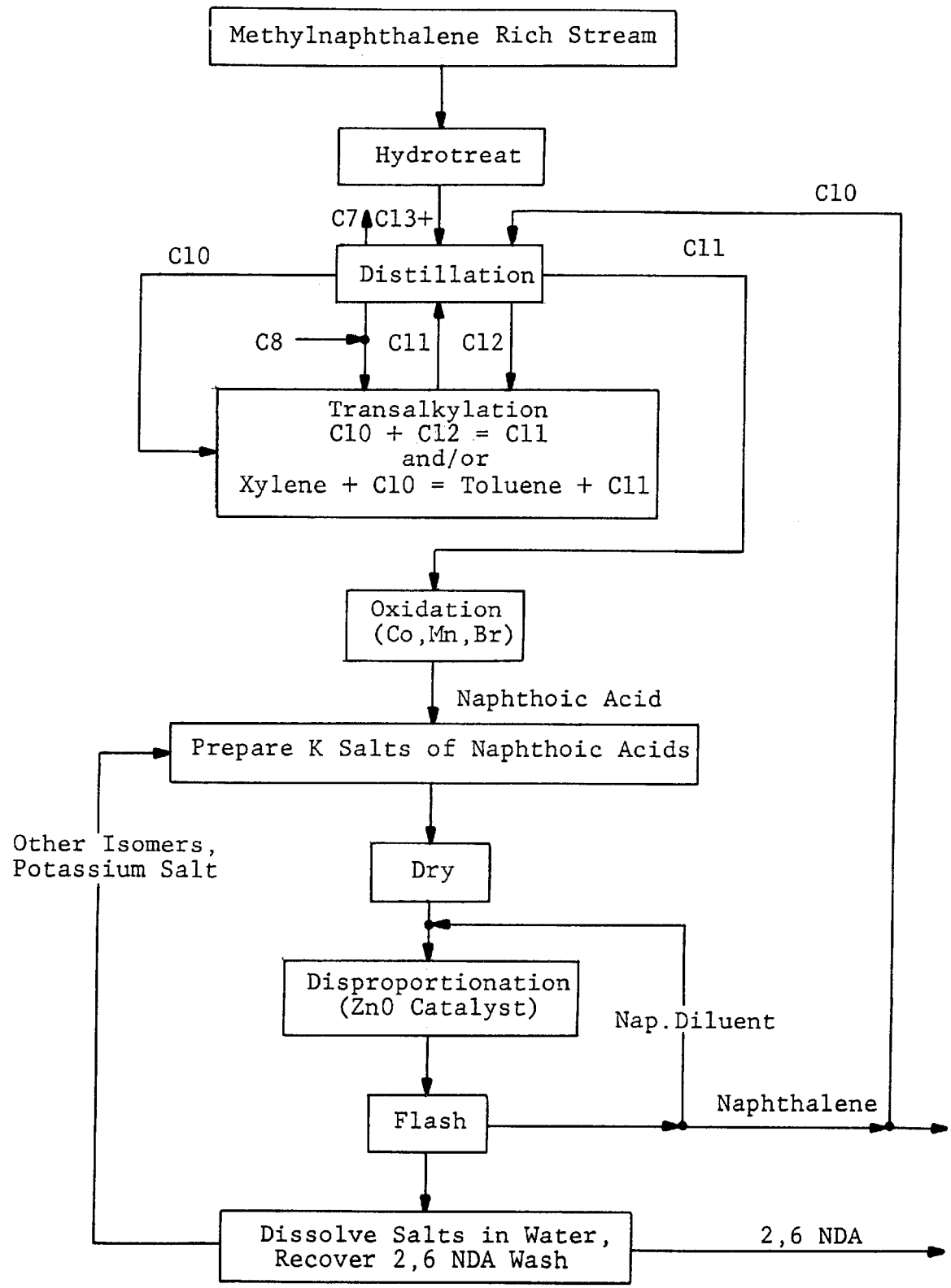
FIG. 4 is a block flow chart showing an optional method of extending the feedstock.

FIG. 4 shows a diagram of a method for integrating a process for extending the feed by transalkylation into the process of this invention.

A suitable temperature for the-transalkylation is about 375 to 555° C., and the preferred range is from about 400 to 450° C. In the preferred embodiment the temperature was about 440° C. The total pressure can be from about 250 to 1000 psig, preferably about 350 to 650 psig. In the example of the preferred embodiment the pressure was about 500 psig. Weight Hourly Space Velocity (WHSV) can be from about 0.5 to 10 per hour, and the preferred range would be about 3 to 8 per hour.

As stated, a useful catalyst for the transalkylation comprises a zeolite. Suitable zeolites include: ZSM-5, Zeolite Y and zeolite Beta. It is known in the art when dimethylnaphthalene is the alkylating agent, conversion is expected to be about 20–30 w per pass over ZSM-5, with high (>90% selectivity) to methylnaphthalene.

A preferred Zeolite Y is Ultrastable Y (USY) described in U.S. Pat. No. 3,449,070, incorporated herein by reference in its entirety. Other types of Y zeolite with higher molar silica to alumina ratios can be used such as SDUSY described in U.S. Pat. No. 5,391,291, incorporated by reference herein the entirety. Catalysts that minimize the buildup of coke and reduce the amount of undesirable by-products are preferred.

In order to provide additional methylnaphthalene, naphthalene can be mixed with xylenes in a ratio of 1 mole of napthalene to 9 moles of mixed xylenes. An abundance of alkyl groups is required for the conversion. Using a SDUSY catalyst (80% zeolite/20% alumina) at 440° C., a WHSV of 5 hr$^{-1}$, a hydrogen partial pressure of 500 psi and a molar hydrogen to feedstock ratio of 2, 45% of naphthalene is converted to methylnaphthalene. Thus transalkylation of the naphthalene in the CLGO can be used to increase the amount of methylnaphthalene obtained to a total of between 60–70%.

In addition to alkylating the "native" naphthalene in the CLGO, FIG. 4 shows how alkylation can be used to extend the feed supply by reacting Henkel reaction product naphthalene with an alkylating agent, such as mixed xylenes or dimethylnaphthalene. For example, in theory, the reaction with dimethylnaphthalene reacts one mole each of naphthalene and dimethylnaphthalene to produce two moles of methylnaphthalene. Methanol could also be reacted with naphthalene to produce methyl naphthalene. Trimethylnaphthalenes(TMN) may also be used as alkylating agents. Methylnaphthalene can be recovered from the transalkylation reactor effluent via distillation, and unreacted DMN and naphthalene can be recycled to the reactor.

Conversion of Methylnaphthalene to Potassium Naphthoate

Methylnaphthalene streams prepared as described above are substantially free of sulfur, but contain hydrocarbon impurities that cannot be readily separated from the methylnaphthalene. These remaining hydrocarbon impurities consist primarily of substituted indanes, which may comprise up to about 15% by weight of the total stream. A key feature of the integrated process of this invention is that it can operate with an impure methylnaphthalene feed stream of this type. This is possible due to a novel combination of steps that convert the impure methylnaphthalene stream to a highly pure potassium naphthoate stream, which is required for the subsequent conversion to 2,6-NDA.

The methylnaphthalene stream is first oxidized with air, using an acetic acid solvent, and a catalyst comprised of cobalt, manganese and bromine. In this step, methylnaphthalene is converted primarily to naphthoic acid, and water is formed as a by-product. A lesser portion of the methylnaphthalene remains unreacted, or is converted to naphthaldehyde, bromonaphthoic acid, and benzene polycarboxylic acids, such as phthalic and trimellitic acids. The substituted indanes that are present as impurities in the feed are also converted to similar benzene polycarboxylic acids.

Acetic acid and water are removed from the oxidation reaction product by evaporation. Benzene polycarboxylic acids, cobalt, manganese, and ionic Br are removed from the remaining molten organic mixture by extraction with water. The mixture is treated with hydrogen by passing the solvent-free stream over a carbon-supported palladium catalyst, converting the bromonaphthoic acid into naphthoic acid and ionic bromine. The ionic bromine created in this step is removed from the mixture by a second extraction with water. Cobalt, manganese and bromine are recovered from these water streams for recycle to the oxidation step.

The remaining molten organic mixture is then contacted with aqueous base, extracting naphthoic acid and converting it to the potassium salt. The remaining organic phase contains methylnaphthalene and naphthaldehyde, both suitable for oxidation to naphthoic acid, and is recycled to the oxidation step.

The overall molar yield of methylnaphthalene to potassium naphthoate is in excess of 90%. Details of the steps that convert the impure methylnaphthalene to potassium naphthoate are discussed below.

In the first step, methylnaphthalene is oxidized to form a crude naphthoic acid stream. Any suitable oxidation process may be employed here. A particularly suitable process is described in U.S. Pat. No. 3,856,855, incorporated by reference herein in the entirety. In the oxidation reaction step of the present invention, a methylnaphthalene stream is introduced into an oxidation reactor, FIG. 2, 14, along with a solvent, catalyst, and an oxygen-containing gas. The methylnaphthalene stream is normally about 85% pure, and contains a mixture of 1-methylnaphthalene and 2-methylnaphthalene, which are oxidized to form 1-naphthoic acid and 2-naphthoic acid, respectively. Both of these acids can be used to make the 2,6NDA product. Suitable solvents for the oxidation reaction include carboxylic acids, with acetic acid being preferred. The catalyst for the oxidation reaction is preferably comprised of cobalt, manganese, and bromine. Additional catalyst components that are known in the art and may improve the rate or selectivity of the reaction include zirconium, hafnium, and cerium. A suitable temperature range for the oxidation is from about 100° C. to 200° C. The preferred temperature range is from about 130° C. to 170° C., preferably about 150° C. The oxidation step is normally run under refluxing conditions in order to remove the considerable heat evolved by the oxidation reactions, therefore the heat balance at the chosen temperature will determine the actual operating pressure. Suitable pressures are in the range of 0 to 400 psig, preferably about 100 to 300 psig. Because the steps following the oxidation allow for the efficient recycle of unreacted methylnaphthalene and intermediate oxidation products, the oxidation need not be carried out under conditions which favor high conversion. This allows lower reaction temperatures, lower concentrations of catalyst and acetic acid solvent, and shorter reaction times, leading to significantly reduced losses of acetic acid due to burning, a lighter colored product, and a significantly lower amount of bromine that is organically bound to the naphthoic acid product.

After the oxidation step, the acetic acid solvent and produced water are removed from the crude naphthoic acid oxidation product via distillation, and steam stripping, as shown in FIG. 2, 19 and 20. Acetic acid is separated from the water by distillation in 25, and recycled to the oxidation reactor. The recovered crude naphthoic acid product is extracted with water in 33 at about 140 to 160° C. This temperature should be above the melting point of the crude mixture of naphthoic acids, but still low enough to minimize solubility of naphthoic acid in the water. This water extraction step significantly reduces the amount of ionic bromine, by-product benzene polycarboxylic acids, and catalyst components in the crude naphthoic acid. These catalyst components are recovered from the water stream 30 in 28 and recycled to the oxidation reactor.

In the hydrodebromination reaction step, FIG. 2,37, crude molten naphthoic acid is treated with hydrogen over a catalyst to substantially reduce the amount of bromine that is organically-bound to the naphthoic acid products formed in the oxidation. This step is necessary to minimize the amount of bromine that is fed to the downstream sections of the process, where the presence of bromine would require more expensive metallurgy. A suitable temperature for the debromination in this process is from about 150 to 320° C., preferably from about 200 to 300° C. Particularly good results are obtained between about 220 and 260° C. A suitable hydrogen partial pressure range is from about 20 to 300 psig, preferably from 50 to 200 psig, and most preferably about 100 psig. Excessive hydrogen partial pressure leads to partial saturation of the aromatic ring structures of naphthoic acid. Suitable catalysts for this reaction include palladium, platinum, rhenium, ruthenium and alloys of these metals with others, for example palladium/silver or palladium/nickel. The preferred catalyst is palladium supported on carbon. Other catalyst support materials could be employed, as long as they are stable under the reaction conditions. Under the preferred conditions, this hydrodebromination step is capable of reducing the amount of bromine that is organically bound to naphthoic acid to less than 25 ppm by weight.

In an example of debromination methods in this field, U.S. Pat. No. 5,292,934, debromination of aromatic carboxylic acid is claimed at temperatures as high as 650–700° F. in the presence of hydrogen and a hydrogenation catalyst. This process requires that a solvent be employed. The present invention operates well at significantly lower temperatures, does not require a solvent to carry out the hydrodebromination, and provides for the removal of acetic acid and oxidation catalyst species which are expected to have a negative effect on the hydrodebromination catalyst lifetime.

Following hydrodebromination, the crude naphthoic acid is again extracted with water in FIG. 2,39 to remove ionic bromine created during the hydrodebromination reaction. The exiting water 34 is routed to the previous water extraction step.

The hydrodebrominated crude naphthoic acid in FIG. 2, 41 is contacted in neutralization reactor 42 with a recycled aqueous solution 48 containing potassium bicarbonate. The potassium bicarbonate reacts with naphthoic acid, converting it to potassium naphthoate and extracting it from the organic phase into the aqueous phase as potassium naphthoate. Water. and carbon dioxide are formed as by-products, and the carbon dioxide is vented in 44 in order to drive the neutralization reaction to completion. The recycled stream 48 also contains some potassium naphthoate, dipotassium salt of 2,3 NDA, and low levels of the potassium salt of 2,6NDA. The molar ratio of basic potassium to naphthoic acid entering the neutralization reactor ranges from about 1 to 1.5, with additional make-up potassium base added in stream 43. The reactor is run with reflux of water to remove the heat of neutralization of naphthoic acid and aid in the removal of carbon dioxide. A suitable temperature for this neutralization step is in the range of 50 to 200° C., preferably about 100 to 150° C. This is also discussed in U.S. patent application Ser. No. 60/151,607 (Attorney's Docket #1595), filed of even date, and incorporated by reference herein in the entirety.

Here it may be noted that U.S. Pat. No. 5,522,905, to Daimler-Benz, incorporated by reference in its entirety, discloses the use of the potassium salt of naphthoic acid, inter alia, as a diesel fuel additive that improves the combustion of soot. The process of the present invention comprises a very efficient method of producing potassium naphthoate, and it would be possible to use the process as described thus far to produce potassium naphthoate or, optionally, have a potassium naphthoate stream exiting the process.

A mixture of organic and aqueous phases exits the neutralization reactor in stream 46 and enters phase separator 47. The organic phase, containing methylnaphthalene and naphthaldehyde, exits the phase separator at 48 and is recycled to the oxidation reactor. The aqueous phase, which contains potassium naphthoate, potassium bicarbonate, dipotassium salt of 2,3 NDA, and low levels of the potassium salt of 2,6NDA, exits at 49.

Disproportionation Reaction

In the integrated process of this invention, the aqueous salt is directed to the disproportionation section in a slurry. Just prior to the disproportionation reactor is a two-stage water removal section. To prepare the feed for the disproportionation reaction, water from the aqueous salt solution of potassium naphthoate is evaporated with hot recycled naphthalene from the disproportionation effluent. The water concentration of the disproportionation feed should be reduced to less than 1000 ppm, to assure optimal yields, and to avoid significant decarboxylation of the disproportionation reaction product.

The disproportionation step is operated in naphthalene diluent, which is subsequently flashed from the solid product. In other work in the art employing disproportionation processes, a salt of naphthoic acid is used as the feed and those processes claim to be operated with a solid feed.

In the preferred embodiment, the aqueous salt of potassium naphthoate is contacted with naphthalene to flash water and is then pumped into the disproportionation reactor as a slurry. The salt of potassium naphthoate can also enter the disproportionation reaction in the solid phase. A diluent system is preferred in the present process for reasons relating to heat transfer, temperature control, etc.

A hydrocyclone, FIG. 2, 57, is used to reduce the solid concentration in the stream feeding the furnace to avoid coking and/or product degradation in the furnace tubes. Just prior to the cyclone, the disproportionation reaction solid ZnO catalyst is added to the slurry in an amount of about 5–20% by weight, FIG. 2, 85. To prepare the feed the crude product in the naphthalene slurry and catalyst are fed into a furnace, FIG. 2, 58 for heating.

Any catalyst that can be used for disproportionation and rearrangement, such as, for example, in the Henkel process could be used in the process of the present invention. Generally, a suitable catalyst would be selected from zinc compounds, cadmium compounds, and mercury compounds in the form of, for example, oxides, halides, sulfates, carbonates, and carboxylates of these metals.

In the present integrated process a zinc compound is preferred. Suitable zinc compounds include zinc halides such as zinc fluoride, zinc chloride, zinc bromide, and zinc iodide; zinc carboxylates such as zinc naphthoate and zinc naphthalene-dicarboxylate; zinc oxide, zinc carbonate; zinc sulfate and mixtures thereof. Note zinc naphthoate includes a 1-isomer, a 2-isomer, and mixtures thereof, and zinc naphthalenedicarboxylate includes a 1,2-isomer, a 1,3-isomer, a 1,4-isomer, a 1,5-isomer, a 1,6-isomer, a 1,7-isomer, a 1,8-isomer, a 2,3-isomer, a 2,6-isomer, a 2,7-isomer, and mixtures thereof. In the preferred embodiment the catalyst employed was ZnO, however Example 4 demonstrates certain advantages using zinc naphthoate.

Suitable temperatures for the disproportionation reaction are in the range of from about 340° C. to 500° C. Better results are observed where the temperature is from about 400° C. to 480° C. The preferred temperature is from about 440° C. to 460° C. This temperature range is, however, very limited. Certain catalysts have the potential to lower temperature and others increase the rate. Raising the temperature generally improves conversion, however decomposition through decarboxylation and tarring becomes more severe at higher temperatures.

Suitable $CO_2$ pressures are from about 200 to 10,000 psi. A more preferred range is from about 350 to 1100 psi. To accelerate the reaction and suppress the occurrence of side reactions the reaction temperature is preferably about 450° C. and the pressure is about 850 psi to 950 psi.

The naphthalene slurry containing the solid particulate salts and ZnO catalyst is fed to the disproportionation reactor at a temperature of about 450° C. and about 850 psi, $CO_2$ headspace, where KNA disproportionates to the dipotasium salt of 2,6NDA and naphthalene. The reaction time can be up to three hours. The optimum residence time is about 1 to 1½ hours.

The reaction medium in the preferred embodiment is naphthalene, but it may be any compound with sufficient thermal stability. It is not restricted to aromatic compounds, however aromatic compounds are suitable.

Examples of suitable solvents include a single compound or mixture of compounds selected from a variety of aprotic polycyclic aromatic compounds, such as, for example, naphthalene, methylnaphthalene, dimethylnaphthalene, diphenyl ether, dinaphthyl ether, terphenyl, anthracene, phenanethrene, and mixtures thereof. The polycyclic aromatic compound is used in an amount of 1 to 6 times, preferably 2 to 4 times, the amount of the starting material based on weight.

The disproportionation reaction produces the salt of the desired 2,6-NDA product, (2,6K2DNA) and naphthalene.

As FIG. 2, 60 and 65 show, the disproportionation reaction is preferably at least two, or even three, stages to push conversion.

The reaction has been found to proceed through a 2,3 dipotassium salt isomer intermediate that forms quickly (5–20 minutes). There was evidence of direct carboxylation to 2,3 K2NDA at about 420° C., which is cooler than the temperature usually considered optimal for 2,6K2DNA production. Conversion of KNDA to 2,3 K2NDA is 20–30%, with no significant 2,6K2DNA or naphthalene product observed.

Using naphthalene as the diluent it has been possible to achieve, for example, about 85% conversion of KNA in 1–2 hours, at 450° C. and 850 psi. Molar selectivity to 2,6K2DNA and 2,3 K2NDA are, for example, about 40% and 5%, respectively. Molar yield to naphthalene is approximately 50%. Coke make is surprisingly low, typically less than 0.1% by weight on a solid product basis, and coke appears to be selectively bound to the ZnO catalyst.

2,6NDA Product Recovery

The disproportionation effluent solids (in naphthalene) consist primarily of 2,6K2DNA, 2,3 K2NDA (isomer intermediate), unreacted KNA, catalyst, and trace coke. After leaving the disproportionation reactor the solid product is washed with water to dissolve the organic salts.

In the next step, shown in greater detail in FIG. 3, the liquid/solid phase product exits the disproportionation reactor where the pressure is, say about 800 to 1100 psi. The liquid/solid phase product exits the disproportionation reactor and enters a tapered bore of decreasing diameter where the liquid/solids mixture is accelerated, causing pressure to drop and part of the liquid to flash, which leads to faster acceleration, pressure drop and liquid flashing. The result of the pressure letdown is that the naphthalene is flashed and the liquid/solid phase becomes gas/solid. The tapered bore can be one of several different types known in the art. Generally it should have an opening at the end receiving the liquid/solid phase product exiting the disproportionation reactor and a tapered bore of a diameter decreasing from the opening extending in the direction of its longitudinal axis terminating in a line which receives the resulting gas/solid phase product and transports it to the first in a series of stripper cyclones.

A cyclone separator uses the centrifugal forces in a confined, high velocity vortex to separate phases of different densities. Cyclones are characterized by large radial pressure gradients that balance the centrifugal forces in the swirling flow. There is a relative vacuum at the center, or core, of the vortex.

The stripper cyclone in the present process is similar to that disclosed in U.S. Pat. No. 4,455,220, incorporated by reference herein in its entirety, but preferably comprises two stages, as shown in FIG. 3. The solids exit the first stripper cyclone through 129 to the lower stripper cyclone. The naphthalene, $CO_2$ and some entrained solids enter a second stage cyclone where additional solid product is separated and returned to the first stripper cyclone. This is discussed in further detail in U.S. patent application Ser. No. 60/151,498 (Attorney's Docket #TH1596), filed of even date, and incorporated by reference herein in its entirety.

The pressure letdown, with the flashing of naphthalene, and separation of gas and solid by stripper cyclones occurs prior to the filtration step. The naphthalene vapor exiting the pressure letdown section is recycled, FIG. 2, 73, used to evaporate water from the aqueous salt of naphthoic acid, and used as a carrier and diluent in the disproportionation reaction. The net naphthalene produced by the disproportionation reaction is either condensed for production of additional methylnaphthalene via transalkylation with dimethylnaphthalene (FIG. 4) or sold to the merchant market, FIG. 2, 72.

Following the pressure letdown section and cyclones, the solid product comprising dipotassium salts of NDA, K2NDA (2,6- and 2,3-isomers), unreacted KNA, catalyst, heavy by-products, and trace coke enter a water wash. The organic salts are dissolved and the liquid is directed to a filter to remove catalyst and coke particles. The ZnO catalyst is recycled and regenerated per the art as described in U.S. Pat. No. 4,263,451, and the references cited therein, incorporated by reference herein in the entirety.

The next step in the process is crystallization of the dipotassium salt. The dipotassium salt of naphthalene dicarboxylic acid resulting from the disproportionation reaction contains at least 15% unconverted feed and intermediates. See Fujishiro, K. and Mitamujra, S. *J. Chem.Soc. Jap.*, 62, 786–790(1989). Crystallization allows sharp separation factors and, indeed, significant purification can be achieved in one step. A desirable feature of the present invention is that the evaporative crystallization step is optimized.

The liquid carrying the mixed organic salts from the disproportionation reaction flows to a two-stage evaporative crystallization section, where the disalt of 2,6NDA (2,6K2DNA) is selectively precipitated.

A recycle stream containing $KHCO_3$ from a subsequent section of the process is sent back through the crystallizers. This recycled $KHCO_3$ is necessary to reach the desired level of purification. The crystallization section rejects a mother liquor stream containing $KHCO_3$, unreacted KNA, and 2,3 K2NDA. Recovery of 2,6K2DNA is approximately 90%, and the purity of the K2NDA leaving the second crystallizer is 99.9%+.

The invention provides the option of a regenerable activated carbon system for purification of 2,6K2DNA (separation from KNA and 2,3 K2NDA). This is discussed in copending U.S. patent application Ser. No. 60/151,589 (Attorney's Docket No.1302), filed of even date, and incorporated by reference herein in its entirety.

If desired, the purified K2NDA slurry is then redissolved with additional clean water and optionally treated with a solid adsorbing agent. This step is optional due to the novel combination of steps providing a relatively pure product and rejecting most impurities. Examples of solid adsorbing agents include activated carbon, active alumina, active magnesia or polymeric adsorbent resins. The use of activated carbon is especially preferred. The amount of the solid adsorbent to be used depends upon the amounts of impurities contained therein. A suitable amount of adsorbent would be in the range of 0.1 to 10 percent by weight, preferably 0.5 to 5 percent by weight, based on the K2NDA. By subjecting an aqueous solution of the dipotassium salt to a solid adsorbent, most residual trace impurities that could affect the color of the final product can be removed.

The next step in the recovery of the dipotassium salt of 2,6-NDA is the precipitation of the disalt with carbon dioxide. The precipitation produces potassium bicarbonate and the solid mono-potassium salt of 2,6-NDA, 2,6-KHNDA. While some impurities are rejected from the 2,6-KHNDA crystals to the mother liquor during the precipitation, the main advantage of this step is that half of the potassium is recovered on each pass for reuse in the disproportionation reaction. The acid used in the neutralization step, carbon dioxide, is cheap and reusable due to its vapor pressure and aqueous solubility. Of most concern in this step is the recovery of 2,6-K2NDA as the mono-salt and the rejection of 2,3-K2NDA from the mono-salt crystals. Example 7 demonstrates the precipitation step.

In the preferred embodiment, the monopotassium salt of 2,6-NDA (KHNDA) is selectively precipitated from an aqueous K2NDA solution (about 20%) at 0–200 psi $CO_2$ pressure, and 0–50° C., for about 30 minutes to 3 hours. Yields of better than 80% have been demonstrated at only 1 atm $CO_2$ pressure. The fact that the precipitation can be done effectively at modest pressure allows for centrifugation of the product without releasing pressure. The centrate contains dissolved potassium bicarbonate, and if activated carbon is used in lieu of crystallization, also contains the 2,3 K2NDA isomer, which is not removed by the regenerable carbon system described herein, but is rejected during the KHNDA precipitation step.

Although it is not shown in the preferred embodiment, the centrate stream can optionally be concentrated via reverse osmosis and then recycled to the second stage of evaporative crystallization. This is discussed in copending U.S. patent application Ser. No. 60/151,497 (Attorney's Docket No. TH1356), filed of even date, and incorporated by reference herein in its entirety.

KHNDA solids are then diluted to 5–10% and reacted for less than an hour, preferably about 20 to 30 minutes at 150° C., under about 50 psi $CO_2$ pressure. What is expected according to what is known in the art is that in this reaction step, two moles of the monopotassium salt of 2,6NDA (KHNDA) disproportionates to form one mole each of 2,6NDA(s), and K2NDA with a maximum yield of about 50%, however we have found, at the conditions noted, the actual measured molar yield is closer to 60–65%. It has been discovered in the present invention that there are evidently conditions for the disproportionation of KHNDA which result in direct neutralization of KHNDA with $CO_2$, effectively increasing the molar yield.

The predicted 50% is calculated by assuming the only reaction is disproportionation. The increased yield is attributed to the discovery of conditions that allow direct neutralization of some of the KHNDA with $CO_2$ and/or $CO_2$ neutralization of the K2NDA to KHNDA, then disproportionation. The reactor effluent from this step is separated with washing to give a 2,6-NDA solid, and a centrate containing predominantly 2,6K2DNA and $KHCO_3$. The centrate is recycled directly to the KHNDA precipitation reactor in the preferred embodiment, but may alternatively be concentrated with a reverse osmosis unit prior to recycle.

Pipeline Reactor

Another key advantage of the present integrated process is that it provides improvements in purification which allow a practical method of reducing potassium to acceptable levels for subsequent polymerization.

The solid 2,6-NDA feed contains from about 60–1000 ppm potassium on a dry basis. It is desirable to reduce the amount of potassium to 50 ppm or less.

The key to obtaining polymer grade product with <50 ppm potassium without using excessive water is the combined use of a 5:1 water wash and a pipeline reactor to drive the reaction to completion. In the water wash a ratio of about 5 parts water is added to 1 part 2,6-NDA solid and reacted at a temperature of about 90 to 180° C., preferably about 150° C. for up to an hour, preferably about 30 minutes. The higher temperature is preferred because it affords higher solids loading.

The 2,6-NDA is then introduced into a reactor of the type known as a pipeline reactor, characterized by plug flow kinectics. In a plug flow reactor very little, if any, back mixing of product with feed occurs, as contrasted with a stirred vessel reactor or pipe loop reactor.

Reactors of the type known in the art as turbulent flow would also be effective.

The temperature in the pipeline reactor should be in the range of 100–200° C. The preferred range is about 140–170° C., with 150° providing good results.

The residence time in the pipeline reactor can vary.

The slurry is reacted at plug flow conditions to drive the KHNDA disproportionation reaction toward completion and to remove trace potassium. In example 9 it was found that the desired results were achieved under plug flow conditions in about 30 minutes to an hour.

The contents of the pipeline reactor is directed to a centrifuge where trace contaminants are removed and recycled back to the KHNDA disproportionation reactor.

The 2,6-NDA is then combined with water, again at about a five fold excess, and the temperature is increased to about 150° C. This second water wash is described in the description of the preferred embodiment in FIG. 2, but could be optional. However, this wash makes it possible to reduce the concentration of potassium to less than 50 ppm. Example 10 demonstrates the reduction of potassium levels to <50 ppm.

The slurry containing the product 2,6-NDA is directed to a last centrifuge to separate the product from the water. The 2,6-NDA solid can be dried by conventional means, or as described, for example, in U.S. Pat. No. 5,292,934 or 5,840,968, incorporated by reference herein. However, where dry handling of the solid product is practiced, particle size control can be critical and the handling of 2,6-NDA particles is difficult and costly.

Therefore, in another aspect of this invention the integrated process for the production of 2,6-NDA can be operated to end with the 2,6-NDA in a water slurry which is convenient for close coupling with a process for making polyethylene naphthalate (PEN), thus avoiding the difficulties associated with product particle size control, drying, and solids handling. 2,6-NDA, present as a solid in an aqueous slurry following purification, is pumped directly into a PEN plant where water is removed during the first esterification reaction with ethylene glycol. Slurry water is removed in the same step that the water of reaction is removed, and the first stage esterification reactor and appurtenances are designed to accommodate the additional water. A PEN process designed to remove the slurry water in addition to the water produced via the transesterification reaction with ethylene glycol should lead to improved PEN polymer with low DEG. This is discussed in copending U.S. application Ser. No. 60/151,603 (Attorney's Docket No.TH1598), filed of even date, and incorporated by reference herein in its entirety.

It should be apparent to those skilled in the art that the present integrated process offers many attractive features not currently available in any process for producing 2,6-NDA.

Inexpensive olefin plant and refinery feedstock

Efficient potassium recycle

Improved post-oxidation hydrodebromination

Solids handling not necessary

Potassium salt springs oxidation impurities

Moderate conditions for the precipitation of KHNDA

Conditions for disproportionation of KHNDA which effectively increase yield

Improvements in reducing potassium level

Direct slurry to a PEN process

Polymer grade naphthalene dicarboxylic acid

The present invention will be more clearly understood from the following examples. It is understood that these examples are presented only to illustrate some embodiments of the invention and are not intended to limit the scope thereof.

EXAMPLE 1

(Oxidation)

This example demonstrates the oxidation of a mixed methylnaphthalene (MN) feedstock to produce a naphthoic acid-containing product suitable for subsequent conversion to 2,6- naphthalene dicarboxylic acid (NDA).

The continuous oxidation of a MN feed was accomplished by feeding a solution comprised of 1-MN, 2-MN, acetic acid, water, cobalt acetate tetrahydrate, manganese acetate tetrahydrate, and aqueous hydrobromic acid through a diptube, into the bottom of a 500 ml Hastalloy C autoclave.

An oxygen containing gas, was coincidentally delivered to the autoclave through the diptube. Liquid level in the autoclave was measured by a conventional dP cell arrangement, and the level was maintained by periodic removal of portion of the autoclave contents by use of an interval timer. Effluent gas from the autoclave was cooled to condense the solvent vapor and the resulting liquid was returned to the autoclave. The reaction temperature and pressure were controlled by conventional means.

In this fashion, a solution containing 1900 g of acetic acid, 100 g water, 500 g of methylnaphthalate, 10.7 g of cobalt acetate tetrahydrate, 31.5 g of manganese acetate tetrahydrate, and 28.6 g of 48% by weight aqueous hydrobromic acid was continuously fed to the autoclave at 9 g/min and the level was maintained to produce a 33 min residence time. Coincidentally, a gas containing 21% oxygen in nitrogen was fed to the autoclave while maintaining a pressure of 400 psig and temperature of 150° C. Under these conditions, 96% mol of the MN was converted to oxidized products and intermediates. Analysis by liquid chromatography indicated a 78% molar yield of naphthoic acid, a 4% molar yield of naphthaldehyde, and smaller amounts of phthalic and trimellitic acids, and other reaction products.

EXAMPLE 2

(Hydrodebromination)

For this example, reactor effluent obtained from a continuous oxidation reaction was subjected to rotary vacuum evaporation at 150° C. and 50 mm Hg pressure to remove acetic acid and water. The remaining solid material was melted and extracted with an equal weight of water at 150° C. Ten grams of the organic layer, containing approximately 0.7% wt organically bound bromine and 0.2% wt ionic bromine, was charged to a stirred 316 stainless steel autoclave, along with 1 gram of 1% wt palladium/carbon catalyst. The gas space of the autoclave was purged with hydrogen, and the pressure was raised to 100 psig with hydrogen. The autoclave was heated rapidly to 100° C. and held at that temperature for at least 10 minutes to assure activation of the catalyst. The autoclave was heated further to 220° C. and held at that temperature for 2 hours. The autoclave was allowed to cool to about room temperature, at which time the excess pressure was vented.

The entire contents of the autoclave was removed and mixed with sufficient aqueous potassium hydroxide to dissolve all of the naphthoic acid and Br-naphthoic acid as the corresponding potassium salts, and toluene to dissolve the remaining organic material, including methylnaphthalene and naphthaldehyde. This mixture was filtered to remove the palladium/carbon catalyst, then separated into organic and aqueous layers. The aqueous layer was acidified with aqueous sulfuric acid, to precipitate the naphthoic acid and Br-naphthoic acid. The precipitate was recovered by filtration, rinsed with water, and vacuum-dried at 100° C. This material was found to contain 34% wt 1-naphthoic acid and 67% wt 2-naphthoic acid by HPLC analysis.

In order to maximize removal of ionic bromine trapped in the precipitate, the material was again neutralized with aqueous potassium hydroxide, acidified with aqueous sulfuric acid, filtered, rinsed with water, and dried. This material was found to contain 24 parts per million by weight (ppmw) bromine by X-ray fluorescence analysis.

EXAMPLE 3
(Henkel)

In a typical experiment the following materials were charged:

TABLE 1

| Chemical name | Grams | Gram moles | % weight of total |
| --- | --- | --- | --- |
| 1- or 2-naphthoic acid (NA) | 30 (91% pure NA) | 0.13 | 32.3 |
| Zinc oxide | 3 grams | 0.037 | 3.2 |
| Naphthalene | 60 grams | 0.47 | 64.5 |

The reaction is performed in a 0.3 liter bolt head autoclave constructed of either stainless steel or hastelloy. After the reactor is purged of air a partial pressure of 500 psig carbon dioxide is supplied. The reactor is heated to 120° C., and depressurized to expel water. The reactor is then pressurized and depressurized with carbon dioxide several times. The reactor is then pressurized with carbon dioxide to 500 psig and heated with a conventional heating mantle to the reaction temperature of 450° C. over the course of one hour. Pressure in the vessel typically rises to between 500 and 1100 psig. The differential between the skin and internal temperature is typically about 50° C. The reaction time is up to three hours. Sampling of the reactor at intermediate intervals is achieved by dip legs which communicate to stainless steel sample vials. At the conclusion of the run, a heating mantle is physically removed, and the temperature drops rapidly.

The cooled reactor and sample vials are disassembled and the contents removed. The cooled reactor product is typically hard, and must be chiseled or drilled from the reactor. Product is then milled to a homogeneous, fine powder. This material is then washed with toluene to remove naphthalene, and after oven drying is analyzed for metals via x-ray, and for composition by means of HPLC and NMR. The conversion and selectivity given below reflect the total weight (molar) fraction of potassium naphthoate converted, and selectivity to NDA based on a stoichiometric expectation of 1 mole NDA from every two moles naphthoic acid. Results are as follows in Table 2:

TABLE 2

| Reaction Temperature, ° C. | Reaction Time, Hours | % Naphthoic Acid Converted | Percent of Theory Selectivity to NDA |
| --- | --- | --- | --- |
| 440 | 2 | 68 | 43 |
| 450 | 1 | 82 | 70 |
| 450 | 2 | 88 | 82 |
| 460 | 2 | 95 | 89 |

Using the table above, it may be seen that conversion is improved by raising the temperature up to and including 460° C.; however experience teaches that decomposition through decarboxylation and tarring becomes more severe at higher temperatures, so that a preferred temperature is more in the neighborhood of 450° C.

In this reaction, zinc oxide is found to be necessary to both promote the reaction and suppress the occurrence of colored matter in the product. The zinc oxide used was obtained as a fine powder, consisting of particles on the order of one micron in diameter. This catalyst may be recovered from the reaction mixture by water washing to remove acid salts. When this was done, the resulting powder was found to contain a small quantity of deposited coke, yet was found to be active when incorporated into a subsequent reaction of the sort described above.

EXAMPLE 4
(Alternative Catalyst)

A more rapid conversion was achieved when the zinc catalyst was formulated as the naphthoate salt. A slurry was made of the following:

TABLE 3

| Substance | Grams | Moles |
| --- | --- | --- |
| Naphthoic Acids | 172 | 1 |
| Zinc Oxide | 40.7 | 0.5 |
| Naphthalene | 210 | 1.6 |

This mixture was then charged to an autoclave and heated to between 200° C. and 300° C. under moderate pressure for one hour. The resulting mass was cooled, pulverized and the naphthalene removed. Yield was essentially 100% of theory of zinc naphthoate. Used as a catalyst, the zinc naphthoate was added as follows:

TABLE 4

| Component | Standard Run - Zinc Oxide | Zinc Napthoate Run |
| --- | --- | --- |
| Napthalene, grams (diluent) | 60 | 60 |
| Potassium Napthoate (KNA), gm | 30 | 30 |
| Zinc Oxide | 3 | 0 |
| Zinc Napthoate (disalt) | 0 | 15 |
| grams naphthoic acid/gram zinc | 10.2 | 15.5 |

At 450° C., conversion was more rapid for zinc naphthoate than zinc oxide, even at a lower total zinc loading. The following results compare with those given above for the zinc oxide catalyzed reaction:

TABLE 5

Zinc Naphthoate Catalyzed Reaction of Potassium Naphthoate at 450° C.

| Reaction time, hours | % Naphthoic Acid Converted | Percent of Theory Selectivity to NDA |
| --- | --- | --- |
| 2 | 98+ | 65 |
| 1 | 96 | 67 |
| 0.5 | 94 | 74 |

From this example it is seen that a shorter residence time is actually favored to prevent losses in selectivity due to decomposition of the products.

EXAMPLE 5

Example 5 is intended to demonstrate the solubility of 2-KNA and 2,6-K2NDA in solutions with varying potassium carbonate concentration. The data was gathered by equilibrating the potassium salts of 2-KNA and 2,6-K2NDA in aqueous solutions of potassium carbonate. The capped jars were contained in water baths to control the temperature and were magnetically stirred to speed the dissolution of the solids. Data derived from the solubility studies are outlined in Table 6. They show that the solubilities of the salts are strongly affected by the background potassium ion concentration via the potassium carbonate concentration. The results indicate that the crystallizations should be run at higher temperatures to take advantange of the widening differential solubilities of the 2-KNA and 2,6- K2NDA salts. The data also demostrate that the solubility of the 2,6-K2NDA salt is only a weak function of temperature so that temperature swing crystallization is not feasible. The data also demosnstrate that some difficulty can be expected if the correct order of addition is not adhered to when making up a solution of these salts from potassium carbonate and aromatic acids due to the significantly lower solubility of the salts in concentrated base solutions.

TABLE 6

| Wt % | 2-KN (wt %) 2,6-K2NDA | | | | Solubility Ratio 2,6-K2NDA/2-KNA | |
|---|---|---|---|---|---|---|
| $K_2CO_3$ | 35° C. | 80° C. | 35° C. | 80° C. | 35° C. | 80° C. |
| 10 | 33.9 | | 13.8 | | 0.41 | |
| 15 | 13.2 | | 6.8 | | 0.52 | |
| 20 | 2.1 | 41.1 | 2.4 | 5.5 | 1.13 | 0.13 |
| 25 | 0.4 | 19.2 | 0.6 | 1.6 | 1.41 | 0.08 |
| 30 | 0.2 | 7.4 | 0.2 | 0.6 | 1.33 | 0.08 |

EXAMPLE 6

(Crystallization)

Crystallizations were performed in a 1 liter, jacketed glass crystallizer with internal dimensions of approximately 4 inches in diameter by 7 inches in height. The vessel had an o-ring sealed bottom valve to allow draining of the crystallizer at the end of the run. Hot oil was circulated through the jacket to maintain the vessel contents at a specified temperature. Stirring shaft speed was controlled with a Lightnin Labmaster stirrer motor. The agitator was a 2.5 inch diameter, 3 bladed, 45 degree pitch impeller. Three segmental baffles were used to aid in suspension of crystals in the vessel. After condensing in a chilled water condenser, evaporated water was collected in a round bottom flask on a balance so that water takeoff rates could be monitored. Pressure in the system was controlled with an absolute pressure regulator connected to a house vacuum line. Feed to the crystallizer was metered with a Beckman HPLC pump through an overhead port. A 100 psig back pressure regulator on the feed line was required to prevent siphoning of the feed when the crystallizer was under vacuum. Filtration of the crystals at the end of the run was done in a 5 inch diameter filter dish that was maintained in an oven at the temperature of the crystallization prior to use.

The crystallizations were performed by adding about 450 g of the mixed feed to form a heel in the crystallizer.

A description of the feed is given in Table 7. No seeds were employed in the crystallization startup. Then, after heating to 85° C., 950 g of feed were added to the vessel with the HPLC pump at about 3–4 g per minute. The hot oil temperature was adjusted, generally in the 160 to 170° C. range, to keep a constant level in the crystallizer at a fixed feed rate. An overhead water takeoff rate of 2 to 3 g per minute was typical. After the run, the crystallizer contents were dumped into a filter dish. Mother liquor from the filtration was then used to reslurry material hung up in the crystallizer before filtering the crystallizer contents through the cake again. The cake was then washed with approximately 200 g of 20% $K_2CO_3$ solution. By using a high ionic strength solution, good displacement washing was obtained without dissolving significant amounts of the cake.

Crystallizations were performed under a single basic set of conditions. These conditions were at 80–85° C. and about 350–400 mm Hg of pressure. Potassium carbonate in the feed was at about 5% to moderate the solubility of the 2,6-K2NDA. A mass balance from a run with 2-KNA and 2,6-K2NDA in the feed is included in Table 7.

TABLE 7

| SX-ID | Grams | Wt % 2,6-K2NDA | Wt % 2-KNA | Description | Feed composition Wt % | |
|---|---|---|---|---|---|---|
| 37-1 | 1110 | 16.1 | 1.78 | Feed | 16.3 | 2,6-K2NDA |
| 37-2 | 190 | 89.15 | 2.66 | Wet cake sample | 1.8 | 2-KNA |
| 37-3 | 334 | 12.64 | 5.19 | Filtrate | 5.1 | $K_2CO_3$ |
| 37-4 | 753 | 1.74 | 0.184 | Crystallizer wash soln. | 76.7 | $H_2O$ |
| 37-5 | 193 | 5.65 | 1.98 | Wash liquor | | |
| 37-7 | 100 | 110.22 | 0.435 | Dry cake | | |
| NA | 200 | | | 25% $K_2CO_3$ wash soln. | | |
| NA | 499 | | | Overhead | | |

EXAMPLE 7

Example 7 demonstrates the precipitation of the disalt of 2,6-NDA to produce KHNDA. A one liter glass vessel previously used in 2,6-K2NDA evaporative crystallizations was modified with the addition of a glass frit to act as a $CO_2$ sparger. Gaseous $CO_2$ was delivered from dry ice in a round bottom flask in a stainless steel can on an electronic balance. The addition of varying amounts of glass wool around the flask allowed the $CO_2$ sublimation rate to be controlled. A 1 psig cracking check valve on the tygon tubing prevented overpressures on the sparger line. When $CO_2$ was noted to be venting from the check valve, which indicated a fouled frit, the sparger tube was switched for one with a clean frit. The solution pH was continuously monitored during runs with a glass electrode mounted in a rubber stopper in a port on top of the glass vessel. For good gas bubble dispersion, the impeller speed was controlled at 500 rpm by a Lightnin Labmaster stirrer motor.

The experimental procedure typically consisted of starting the precipitation experiment with about 500 g of feed typically containing 20% 2,6-K2NDA before being adjusted to a pH of 10 by adding KOH or 2,6-K2NDA as required. The $CO_2$ flask was filled with dry ice and allowed to come to a steady state sublimation rate before being attached to the sparger line. A balance was used to monitor the weight loss from the $CO_2$ flask and track the $CO_2$ addition rate. The solution temperature was typically held at 30–40° C. by circulating hot oil through the precipitator jacket. After starting the $CO_2$ flow to the precipitation vessel, the amount of $CO_2$ delivered and solution pH was recorded periodically. When the pH fell to a steady value, the experiment was terminated and solids were filtered from the magma in a filter dish. Approximately 500 g of wash water was added to the precipitator to recover any solid material that was hung up in the vessel. This liquid was then filtered through the cake to displace any soluble 2,6-K2NDA from the cake. Samples of the feed, mother liquor, and wash liquor were than taken for HPLC analysis. The cake was dried and analyzed for potassium by x-ray florescence or ion chromatography. Analysis for 2,3-K2NDA was via HPLC at high 2,3-K2NDA levels and with IC chromatography for low levels of 2,3-K2NDA in the presence of high levels of 2,6-K2NDA. In both cases, UV detection was used.

Results from a series of precipitation experiments are summarized in Table 8 where gravimetric yield is reported along with a yield computed by difference from the soluble 2,6-K2NDA in the aqueous mother liquor and wash water. The base run conditions are 20% 2,6-K2NDA feed concentration, a 2 hour run time, an initial pH of 10, a 35° C. run temperature, and a $CO_2$ delivery rate of about 0.6 $CO_2$/min. Other runs are described in Table 8 by what variable differentiated them from the base run conditions. 2,6-KHNDA molar yields of at least 80% under baseline conditions are demonstrated. In general, there is good agreement between the gravimetric yield and the yield computed by difference from mother liquor and washing losses. A run under higher temperature conditions (−178) where the solubility of $CO_2$ is lower and the solubility of 2,6-KHNDA is higher generated a lower yield as did run (−186) conducted under vacuum so that the $CO_2$ pressure was limited to 0.5 atm.

Knowing that it is possible under certain circumstances that the di-salt from the disproportionation reaction could contain excess potassium carbonate, runs −172 and −175 were performed with 7.5 and 15 mole percent potassium carbonate added to the solution on a 2,6-K2NDA basis in an effort to determine if this would have an effect on the recovery of the 2,6-KHNDA. These runs produced significantly lower yields of solids indicating that at atmospheric $CO_2$ pressures, the yield could be impacted by excess carbonate.

In runs −185 and −191, the rejection of 2,3-K2NDA from the mono-salt crystals was quite efficient as significant amounts of the material were rejected. Levels in the final cake were below the 2000 ppm HPLC detection limit. This rejection is as good as or better than that achieved with crystallization of the di-potassium salt of NDA.

These runs demonstrate that the monopotassium salt of 2,6-NDA can be recovered at about 80% yield at atmospheric pressure if the temperature is kept at about 35° C. and a batch residence time of about 2 hours is employed.

feed K2NDA to KHNDA is computed from the difference between the concentrations of NDA in the feed and product solution. The formation of bicarbonate from the added $CO_2$ and its diluting effect on the mother liquor is taken into account in the yield calculation. Results are recorded in Table 9:

TABLE 9

|  | % K2NDA | pH | Conv. (%) |
|---|---|---|---|
| 40° C./3 hr. | | | |
| 152-1 | 19.1 | Feed | NA |
| 153-1 | 4.29 | 7.66 | 76 |
| 153-2 | 3.98 | 7.66 | 77 |
| 153-3 | 6.46 | 8.07 | 65 |
| 10° C./3 hr | | | |
| 155-1 | 19.5 | Feed | NA |
| 155-2 | 19.1 | Feed | NA |
| 155-3 | 1.52 | 7.50 | 90 |
| 156-1 | 1.40 | 7.60 | 90 |

EXAMPLE 9

Example 9 describes the method used to first disproportionate KHNDA to 2,6-NDA and to reduce the concentration of potassium in the NDA solid product. In example 9 a feed slurry of between 5 and 7.5 wt % KHNDA in water was made up and disproportionated at temperatures between 95 and 135° C. for approximately 0.5 to 2.0 hours. The resulting solid was filtered. The filter cake was then hot water washed with an approximately 5 fold excess of water that was kept at reaction temperature. The solids were then dried and analyzed for potassium by x-ray fluorescence (XRF). These

TABLE 8

| LR 23166- | Case | NDA (weight %) | | | NDA recovery (%) | | | NDA % Yield |
|---|---|---|---|---|---|---|---|---|
| | | Feed | ML | Wash | ML | Wash | Cake | |
| 166 | Short Run (1 hr) | | | | | | | 71 |
| 168 | Baseline | 17.5 | 2.81 | 1.54 | 8.6 | 9.2 | 82.2 | 83 |
| 169 | Fast $CO_2$ (5 g/m) | 17.5 | 9.33 | 2.26 | 40.3 | 13.2 | 46.6 | 48 |
| 172 | $CO_3$ added (7.5%) | 17.3 | 4.70 | 1.90 | 19.4 | 12.0 | 68.6 | 72 |
| 175 | $CO_3$ added (15%) | 17.0 | 5.34 | 1.88 | 21.7 | 12.0 | 66.3 | 69 |
| 176 | Long Run (3 hr) | 18.1 | 2.64 | 1.40 | 7.6 | 9.4 | 83.0 | 84 |
| 178 | High Temp (50° C.) | 18.1 | 4.74 | 2.08 | 14.7 | 11.8 | 73.6 | 74 |
| 180 | 10% Slurry | 18.1 | 3.75 | 0.97 | 16.6 | 5.8 | 77.6 | 65 |
| 183 | Baseline | 18.1 | 3.42 | 1.55 | 9.7 | 8.4 | 81.8 | 82 |
| 185 | 5% 2,3 K2NDA | 18.1 | 0.17 | 0.02 | 0.6 | 0.1 | 99.3 | 96 |
| 186 | Low press (0.5 atm) | 18.1 | 8.10 | 2.33 | 31.4 | 12.9 | 55.7 | 57 |
| 188 | Baselin | 16.9 | 4.57 | 2.08 | 12.8 | 12.7 | 74.5 | 76 |
| 191 | 5% 2,3-K2NDA | 17.1 | 10.26 | 1.44 | 43.8 | 13.7 | 42.6 | 55 |

EXAMPLE 8

Example 8 demonstrates the $CO_2$ precipitation of a 20% aqueous solution of K2NDA to produce KHNDA. The reaction was carried out using about 1 atm of $CO_2$ The pH of the K2NDA was adjusted to 10 in a continuous stirred tank reactor (CSTR). The CSTR was fed with a high pressure liquid chromatography (HPLC) pump and jacketed with glycol to control temperature. The vessel had baffles and a 3 blade impeller to circulate the mother liquor. A fritted sparge tube was used to disperse the $CO_2$ bubbles. At 3 hours residence time, fouling was nota problem. The conversion of results are shown in Table 10. The solid was then reslurried in water in a 5 to 1 water to solid ratio and kept at 95° C. for 0.5 hours. The solids were then filtered at temperature, dried, and again analyzed for potassium by XRF and/or by a more sensitive plasma jet analysis (ICP). Again, the results are recorded in Table 10. In some cases, a second reslurry of the NDA solids, with conditions identical to the first reslurry, was carried out. This example employs kinetics which are expected in a pipe line or turbulent flow, or a batch reactor, or a plug flow reactor. From example 9 it is clear that conditions can be found that will lead to 2,6-NDA with less than 50 ppmw potassium present.

TABLE 10

| | Feed | | NDA K+ (ppmw)*, | | | | Reslurry #1 (5/1 water to solid) | | | Reslurry #2 (5/1 water to solid) | |
|---|---|---|---|---|---|---|---|---|---|---|---|
| | Temp. °C. | Res. Time | KHNDA (% W) | ** after water wash | | Temp °C. | Res. Time | K+ (ppmw)** | | Temp (°C.) | Res. Time | K+ (ppmw) |
| 9-1 | 135 | 1.0 hr | 7.5 | 73–140 | 9-1a | 95 | 0.5 hr | 80–150 | 9-1b | 95 | 0.5 hr | 54–109 |
| 9-2 | 135 | 2.0 hr | 7.5 | 71–140 | 9-2a | 95 | 0.5 hr | 57–106 | 9-2b | 95 | 0.5 hr | ?–105 |
| 9-3 | 135 | 1.0 hr | 5 | 21–74 | 9-3a | 95 | 0.5 hr | 15–36 | 9-3b | 95 | 0.5 hr | 9–45 |
| 9-4 | 95 | 1.0 hr | 5 | 1300*** | 9-4a | 95 | 0.5 hr | 8–42 | | | | |
| 9-5 | 95 | 1.0 hr | 5 | 520 | 9-5a | 95 | 0.5 hr | 49**** | | | | |
| 9-6 | 95 | 0.5 hr | 5 | 3800 | 9-6a | 95 | 0.5 hr | 46 by ICP | | | | |
| 9-7 | 95 | 1.0 hr | 5 | 400 | 9-7a | Amb | 0.5 hr | 79 by ICP | | | | |

*K+ after approximately 5/1 water wash of filter cake at reaction temperature
**Also real K+ number is closer to the higher number in the bracket; confirmed by ICP on prior runs
***Filter not kept at reaction temperature
****XRF without BCK subtraction = high on the numbers

EXAMPLE 10

Example 10 demonstrates the preferred conditions for disproportionating KHNDA to 2,6-NDA and K2NDA with higher solids loading and then reducing the potassium level in the resulting solid 2,6-NDA to below 50 ppmw. The residence time for the disproportionation reaction was from 30 minutes to 1 hour and carried out at 100° C. The KHNDA slurry was made up at 8 to 10 wt % for this example. For the first 5 experiments listed in Table 11, the disproportionation was assisted by $CO_2$. After the disproportionation reaction the solid was filtered at reaction temperatures. The filter cake was then hot water washed with approximately a 5 fold excess of water and was kept at reaction temperatures. The NDA solid was then dried and analyzed by XRF. The results are given in Table 11. Selected NDA samples were then slurried in water in a 5 to 1 water to NDA ratio and reacted/soaked for 0.5 hours at 150° C. The samples were then filtered, dried and analyzed by XRF. The results are reported in Table 11. Clearly the example shows that NDA with less the 50 ppmw potassium is achievable.

TABLE 11

| | | | | | K+ (ppmw) | Reslurry 5/1 water to solid | | |
|---|---|---|---|---|---|---|---|---|
| | $CO_2$ Assisted 150 psig System | Temp. °C. | Res. Time | Feed KHNDA (% W) | After About 5:1 Hot $H_2O$ Wash | Temp (°C.) | Res. Time | K+ (ppmw) W/o Background Subtraction |
| 10-1 | Yes | 150 | 0.5 hr | 8 | 69 | 150 | 0.5 hr | <40 |
| 10-2 | Yes | 150 | 0.5 hr | 9 | 630 | | | |
| 10-3 | Yes | 150 | 1.0 hr | 9 | 280 | | | |
| 10-4 | Yes | 150 | 1.0 hr | 9 | 290 | | | |
| 10-5 | Yes | 150 | 1.0 hr | 10 | 330 | 150 | 0.5 hr | <33 |
| 10-6 | No | 150 | 1.0 hr | 8 | 320 | 150 | 0.5 hr | <45 |
| 10-7 | No | 150 | 1.0 hr | 9 | 290 | | | |

We claim:

1. An integrated process: for producing 2,6-naphthalene dicarboxylic acid using methylnaphthalene as the feedstock which comprises:

a) Reacting a hydrocarbon stream containing predominantly methylnaphthalene with an oxygen-containing gas in the presence of a suitable solvent and an oxidation catalyst to form a crude product mixture of naphthoic acid, wherein said crude product naphthoic acid remains dissolved in the solvent;

b) Recovering said crude product midxture of isomers by evaporation of solvent and washing said crude product naphthoic acid with water;

c) Debrominating said crude product naphthoic acid (NA) by passing over a supported catalyst selected from Group VIII in the presence of hydrogen, and water washing said crude debrominated product naphthoic acid;

d) Contacting said crude, debrominated product naphthoic acid with an aqueous basic potassium salt to extract pure naphthoic acid as the aqueous potassium salt of naphthoic acid;

e) Separating said aqueous potassium salt of naphthoic acid from the remaining. organic liquid and recycling said organic liquid to step a);

f) Contacting said aqueous potassium salt of naphthoic acid with naphthalene vapor, adding a solid disproportionation catalyst, and removing water by evaporation to form a slurry of solid potassium salt of naphthoic acid and. catalyst suspended in liquid naphthalene;

g) Reacting said slurry in the presence of carbon dioxide to convert said solid potassium salt of naphthoic acid to liquid naphthalene and solid dipotassium salt of 2,6-naphthalene dicarboxylic acid;

h) Reducing the pressure to vaporize the naphthalene, separating the solids from the naphthalene vapor, recycling a portion of the naphthalene to step f), and recovering the remainder as a product, or methylating the naphthalene via direct alktylation or transalkylation to provide additional methylnaphthalene feed for step a);

i) Contacting the solids with water to create a mixture of aqueous potassium salts comprising the potassium salt of naphthoic acid and the dipotassium salts of 2,6-naphthalene dicarboxylic acid and its isomers and solid catalyst;

j) Separating the solid catalyst from the mixture of aqueous potassium salts and recycling said catalyst to step f);

k) Adding aqueous potassium bicarbonate to the mixture of aqueous potassium salts and evaporating a portion of the water to selectively crystallize the dipotassium salt of 2,6-naphthalene dicarboxylic acid as a solid, separating said solid, and recycling the remaining liquid to step d);

l) Dissolving said dipotassium salt of 2,6-naphthalene dicarboxylic acid in water;

m) Optionally passing said aqueous dipotassium salt of 2,6-naphthalene dicarboxylic acid through an activated carbon bed to remove impurities;

n) Contacting said aqueous dipotassium salt of 2,6-naphthalene dicarboxylic acid with carbon dioxide to create a mixture precipitated solid monopotassium salt of 2,6-naphthalene dicarboxylic acid and aqueous potassium bicarbonate, separating said solids, and recycling the aqueous potassium bicarbonate to step k);

o) Contacting the solid monopotassium salt of 2,6-naphthalene dicarboxylic acid with water, optionally in the presence of carbon dioxide, to form solid 2,6-naphthalene dicarboxylic acid, aqueous dipotassium salt of 2,6-naphthalene dicarboxylic acid, and potassium bicarbonate;

p) Separating the solid 2,6-naphthalene dicarboxylic acid and recycling the liquid containing aqueous dipotassium salt of 2,6-naphthalene dicarboxylic acid and potassium bicarbonate to step n);

q) Contacting solid 2,6-naphthalene dicarboxylic acid with water in a pipe reactor to remove traces of potassium ion impurity;

r) Separating solid 2,6-naphthalene dicarboxylic acid and recycling water to step o);

s) Washing the solid 2,6-naphthalene dicarboxylic acid with water;

t) Separating the water from the solid, producing wet polymer grade 2,6-naphthalene dicarboxylic acid, and recycling most of the water to step q);

u) Drying solid 2,6-naphthalene dicarboxylic acid by conventional means, or optionally feeding as an aqueous slurry to a process for making polyethylene naphthalate, optionally adding additional water if necessary.

2. The process of claim 1 wherein the source of the methylnaphthalene is cracked light gas oil.

3. The process of claim 2 further comprising hydrotreating the cracked light gas oil and afterward distilling the cracked light gas oil to provide the methylnaphthalene.

4. The process of claim 2 further comprising distilling the cracked light gas oil to provide methylnaphthalene and afterward hydrotreating the methylnaphthalene.

5. The process of claim 3 which further comprises hydrotreating the cracked light gas oil to reduce ppm sulfur to less than 10 ppm.

6. The process of claim 1 wherein said oxidation step (a) can tolerate a purity of methylnaphthalene of 85–90%.

7. The process of claim 1 further comprising an additional source of methylnaphthalene feed via transalkylation.

8. The process of claim 1 (a) wherein the oxidation takes place at a temperature of from about 100° C. to about 160° C.

9. The process of claim 8 where the oxidation takes place at a temperature of from about 140° C. to 155° C.

10. The process of claim 1 (a) wherein the solvent is an aliphatic $C_2$ to $C_6$ monocarboxylic acid.

11. The process of claim 10 wherein the solvent is selected from the group consisting of acetic acid, propionic acid, n-butyric acid, isobutyric acid, n-valeric acid, trimethylacetic acid, and caproic acid.

12. The process of claim 1 wherein the solvent is acetic acid.

13. The process of claim 1 wherein said oxidation catalyst comprises cobalt, bromine, and manganese-containing compounds.

14. The process of claim 13 wherein the oxidation catalyst comprises
   a. a cobalt compound soluble in acetic acid under reaction conditions;
   b. a manganese compound soluble in acetic acid under reaction conditions; and
   c. bromine or a bromine compound in quantities meeting the following requirements:

$$3.0 \leq X+Y+Z \leq 8.0$$
   $$0.5 \leq Z/(X+Y) \leq 2.0$$
   $$0.2 \leq X/Y \leq 8$$

wherein
   x represents the amount of cobalt contained in said cobalt compound in terms of parts by weight per 100 parts by weight methylnaphthalene,
   Y represents the amount of manganese contained in said manganese compound in terms of parts by weight per 100 parts of methylnaphthalene, and
   Z represents the amount of the bromine contained in said bromine or bromine compound in terms of parts by weight per 100 parts by weight of methylnaphthalene.

15. The process of claim 13 further comprising additional catalyst components selected from zirconium, hafnium and cerium.

16. The process of claim 13 wherein the catalyst comprises cobalt acetate tetrahydrate, manganese acetate tetrahydrate, and aqueous hydrobromic acid.

17. The process of claim 1 (a) wherein the oxidation takes place at about 145 to 160° C. and 250–350 psi.

18. The process of claim 1 (b) wherein the crude product naphthoic acid dissolved in solvent is recovered by evaporation and washing wherein the evaporation further comprises a series of distillation columns.

19. The process of claim 18 wherein said crude product naphthoic acid in solvent is directed to a first distillation column where acetic acid is taken off the top and crude product naphthoic acid exits the bottom.

20. The process of claim 19 which further comprises directing the acetic acid taken off the top to a second distillation column where waste water is separated off the top and recovered acetic acid exits the bottom and is recycled.

21. The process of claim 19 which further comprises directing the crude product mixture which exits the bottom to a second distillation column where, in the presence of steam, additional acetic acid and water are separated off the top and directed to the second distillation column for acetic acid, and said crude product mixture exits the bottom.

22. The process of claim 21 wherein the temperature of the exiting crude product is from about 145–155° C.

23. The process of claim 1 (c) comprising debromination of the crude product naphthoic acid which further comprises passing the crude product naphthoic acid over a Group VIII catalyst with no solvent at a temperature of from about 220–260° C. and hydrogen pressure of 50 to 200 psi.

24. The process of claim 23 wherein the catalyst is palladium on a carbon support.

25. The process of claim 23 wherein the temperature is about 220° C. and the pressure is about 100 psi.

26. The process of claim 23 further comprising passing the debrominated crude product naphthoic acid through a means for aqueous extraction which recycles water.

27. The process of claim 26 further comprising the bromine species in the crude product exiting the means for aqueous extraction being less than 50 ppm.

28. The process of claim 1 (d) wherein the debrominated crude product naphthoic acid is contacted with an aqueous basic potassium salt in 0–50% molar excess.

29. The process of claim 28 wherein the aqueous basic potassium salt is potassium hydroxide.

30. The process of claim 28 further comprising heating the mixture to about 80–120° C. to drive off $CO_2$.

31. The process of claim 1 (f) further comprising reducing the amount of water to less than 1000 ppm.

32. The process of claim 1 (f) wherein the naphthalene vapor comprises recycled disproportionation reactor effluent.

33. The process of claim 1 (f) which further comprises optionally passing the slurry of solid potassium salt of naphthoic acid and naphthalene through a hydrocyclone to reduce solids concentration in the stream.

34. The process of claim 1 (f) wherein the solid catalyst comprises a disporportionation catalyst selected from the group consisting of compounds of zinc and cadmium.

35. The process of claim 34 wherein the disproportionation catalyst is selected from the group consisting of zinc oxide, zinc iodide, zinc chloride, zinc sulfate, zinc phosphate, zinc carbonate, zinc acetate, zinc benzoate, zinc phthalate, zinc isophthalate, zinc naphthoate, and zinc terephthalate.

36. The process of claim 35 wherein the disproportionation catalyst is ZnO.

37. The process of claim 35 wherein the disproportionation catalyst is zinc naphthoate.

38. The process of claim 1 (g) wherein the slurry is reacted in the presence of carbon dioxide which further comprises the reaction taking place in a disproportionation reactor at a temperature of from about 400 to 480° C. and about 300 to 1200 psi, $CO_2$ headspace for about 1 to 1½ hours to produce 2,6 potassium salts of naphthalene dicarboxylic acid in naphthalene, 2,3-dipotassium salt of naphthalene dicarboxylic acid unreacted potassium salt of naphthoic acid, catalyst, and trace coke.

39. The process of claim 38 further comprising repeating the reaction in the disproportionation reactor at least once in an additional stage to increase conversion.

40. The process of claim 38 wherein the temperature is 450° C., the pressure is 850 psi, the time is 1–2 hours.

41. The process of claim 1 (k) further comprising optionally having two stages of evaporative crystallization with a centrifuge interstage.

42. The process of claim 1 (k) wherein during the evaporative crystallization of the dipotassium salt of naphthalene dicarboxylic acid is selectively precipitated and a part of the stream containing $KHCO_3$, unreacted potassium salt of naphthoic acid, and 2,3-dipotassium salt of naphthalene dicarboxylic acid is separated.

43. The process of claim 42 wherein the recovery of dipotassium salt of naphthalene dicarboxylic acid is approximately 90%.

44. The process of claim 41 wherein evaporative crystallization occurs in two stages and the purity of the dipotassium salt of naphthalene dicarboxylic acid leaving the reactor redissolved in water is 99.9%+.

45. The process of claim 1 (n) wherein the monopotassium salt of 2,6-naphthalene dicarboxylic acid, is selectively precipitated at 0–200 psi $CO_2$ pressure and 0–50° C.

46. The process of claim 45 further comprising centrifuging the precipitate.

47. The process of claim 1 (o) wherein said monopotassium salt of 2,6-naphthalene dicarboxylic acid solids are disproportionated into 2,6-naphthalene dicarboxylic acid and dipotassium salt of naphthalene dicarboxylic acid by reacting said monopotassium salt of 2,6-naphthalene dicarboxylic acid solids, diluted in 5–10% water at about 150° C. under about 50 psi $CO_2$ pressure.

48. The process of claim 45 further comprising centrifuging the product to give a 2,6-naphthalene dicarboxylic acid slurry and a centrate containing 2,6 dipotassium salt of naphthalene dicarboxylic acid and $KHCO_3$.

49. The process of claim 48 further comprising recycling the centrate.

50. The process of claim 48 further comprising optionally concentrating the centrate by reverse osmosis prior to recycling.

51. The process of claim 48 further comprising directing the 2,6-naphthalene dicarboxylic acid in a slurry to a-pipe reactor to drive the reaction to completion and/or remove residual potassium ions.

52. The process of claim 51 further comprising washing the product in a water wash having a 5:1 ratio of water to product.

53. The process of claim 52 resulting in a 2,6-naphthalene dicarboxylic acid product with <50 ppm potassium.

54. The process of claim 52 further comprising drying the 2,6-naphthalene dicarboxylic acid product by conventional drying technology.

55. The process of claim 52 further comprising directly slurrying the 2,6-naphthalene dicarboxylic acid product into a process for making polyethylene naphtahalate (PEN).

56. The process of claim 1 for preparing potassium naphthoate.

* * * * *